(12) United States Patent
Sato et al.

(10) Patent No.: US 7,163,807 B2
(45) Date of Patent: Jan. 16, 2007

(54) NUCLEIC ACID SEQUENCES ENCODING MODIFIED PREPRO PEPTIDES OF AN ALKALINE PROTEASE

(75) Inventors: Tsuyoshi Sato, Haga-gun (JP);
Mitsuyoshi Okuda, Haga-gun (JP);
Yasushi Takimura, Haga-gun (JP);
Nobuyuki Sumitomo, Haga-gun (JP);
Masafumi Nomura, Wakayama (JP);
Tohru Kobayashi, Haga-gun (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 11/318,576

(22) Filed: Dec. 28, 2005

(65) Prior Publication Data

US 2006/0105428 A1  May 18, 2006

Related U.S. Application Data

(62) Division of application No. 10/456,479, filed on Jun. 9, 2003, now Pat. No. 7,101,698.

(30) Foreign Application Priority Data

Jun. 26, 2002 (JP) ............................. 2002-186387
Oct. 18, 2002 (JP) ............................. 2002-304232

(51) Int. Cl.
*C12N 9/52* (2006.01)
*C12N 15/57* (2006.01)
*C12N 15/62* (2006.01)
*C12N 15/74* (2006.01)

(52) U.S. Cl. ................ 435/69.7; 435/219; 435/252.31; 435/320.1; 435/471; 536/23.5

(58) Field of Classification Search ..................... None
See application file for complete search history.

(56) References Cited

U.S. PATENT DOCUMENTS

| 5,891,701 A | 4/1999 | Sloma et al. |
| 6,376,227 B1 | 4/2002 | Takaiwa et al. |
| 6,759,228 B1 | 7/2004 | Takaiwa et al. |
| 6,803,222 B1 | 10/2004 | Hatada et al. |
| 2003/0022351 A1 | 1/2003 | Hatada et al. |

OTHER PUBLICATIONS

K. Saeki, et al., Biochemical and Biophysical Research Communications, vol. 279, No. 2, pp. 313-319, "Novel Oxidatively Stable Subtilisin-Like Serine Proteases From Alkaliphilic Bacillus Spp.: Enzymatic Properties, Sequences, and Evolutionary Relationships", 2000.

*Primary Examiner*—Nashaat T. Nashed
*Assistant Examiner*—William W. Moore
(74) *Attorney, Agent, or Firm*—Oblon, Spivak, McClelland, Maier & Neustadt, P.C.

(57) ABSTRACT

The present invention relates to genes expressing an alkaline protease having a prepro sequence, vectors containing the same, and transformants containing said vector. The present invention also relates to a method for producing an alkaline protease.

6 Claims, 3 Drawing Sheets

```
KP43    1:MRKKKKVFLSVLSAAAILSTVALSNPSAGGARNFDLDFKGIQTTTDAKGFSKQGQTGAAA 60
KP9860  1:MRKKKV-FLSVLSAAAILSTVALNNPSAGDARTFDLDFKGIQTTTDVSGFSKQRQTGAAA 59
KP9865  1:MRKKKKVFLSVLSAAAILSTVALSNPSAGGARNFDLDFKGIQTITDAKGFSKQGQTGAAA 60
          *****..****************.*****.**.**********.**..*****.******

KP43    61:FLVESENVKLPKGLQKKLETVPANNKLHIIQFNGPILEETKQQLEKTGAKILDYIPDYAY 120
KP9860  60:FLVESENVKLLKGLLKKLETVPANNKLHIVQFNGPILEETKQKLETTGAKILDYIPDYAY 119
KP9865  61:FLVESENVKLPKGLQKKLETVPANNKLHIVQFNGPILEETKQQLEKTGAKILDYIPDYAY 120
          **********.***.**************.*************.**.************

KP43    121:IVEYEGDVKSATSTIEHVESVEPYLPIYRIDPQLFTKGASELVKAVALDTKQKNKEVQLR 180
KP9860  120:IVEYEGDVQSKVRSIEHVESVEPYLPKYKIDPQLFTKGASTLVKALALDTKQNNKEVQLR 179
KP9865  121:IVEYEGDVKSATSTJEDVESVEPYLPIYRIDPQLFTKGASELVKAVALDTNQKNKEVQLR 180
          ********.*....**.**********.*.************.****.****.*.*******

KP43    181:GIEQIAQFAISNDVLYITAKPEYKVM                                 206
KP9860  180:GIEEIAQYVASNDVHYITAKPEYKVM                                 205
KP9865  181:GIEQIAQFATSNDVLYITAKPEYKVM                                 206
            ***.***...****.***********
```

Fig. 1

```
KP43     1:MRKKKKVFLSVLSAAAILSTVALSNPSAGGARNFDLDFKGIQTTTDAKGFSKQGQTGAAA 60
KP9860   1:MRKKKV-FLSVLSAAAILSTVALNNPSAGDARTFDLDFKGIQTTTDVSGFSKQRQTGAAA 59
KP9865   1:MRKKKKVFLSVLSAAAILSTVALSNPSAGGARNFDLDFKGIQTITDAKGFSKQGQTGAAA 60
           *****..******************.*****.**.**********.**...*****.******

KP43    61:FLVESENVKLPKGLQKKLETVPANNKLHIIQFNGPILEETKQQLEKTGAKILDYIPDYAY 120
KP9860  60:FLVESENVKLLKGLLKKLETVPANNKLHIVQFNGPILEETKQKLETTGAKILDYIPDYAY 119
KP9865  61:FLVESENVKLPKGLQKKLETVPANNKLHIVQFNGPILEETKQQLEKTGAKILDYIPDYAY 120
           **********.***.**************.************.**.*************

KP43   121:IVEYEGDVKSATSTIEHVESVEPYLPIYRIDPQLFTKGASELVKAVALDTKQKNKEVQLR 180
KP9860 120:IVEYEGDVQSKVRSIEHVESVEPYLPKYKIDPQLFTKGASTLVKALALDTKQNNKEVQLR 179
KP9865 121:IVEYEGDVKSATSTIEDVESVEPYLPIYRIDPQLFTKGASELVKAVALDTNQKNKEVQLR 180
           ********.*....**.*********.*.************.****.****.*.*******

KP43   181:GIEQIAQFAISNDVLYITAKPEYKVM                                 206
KP9860 180:GIEEIAQYVASNDVHYITAKPEYKVM                                 205
KP9865 181:GIEQIAQFATSNDVLYITAKPEYKVM                                 206
           ***.***...****.************
```

Fig. 2 a

```
KP43    1:NDVARGIVKADVAQSSYGLYGQGQIVAVADTGLDTGRNDSSMHEAFRGKITALYALGRTN 60
KP9860  1:NDVARGIVKADVAQSSYGLYGQGQIVAVADTGLDTGRNDSSMHEAFRGKITALYALGRTN 60
KP9865  1:NDVARGIVKADVAQSSYGLYGQGQIVAVADTGLDTGRNDSSMHEAFRGKITALYALGRTN 60
E-1     1:NDVARGIVKADVAQNNYGLYGQGQVVAVADTGLDTGRNDSSMHEAFRGKITALYALGRTN 60
Ya      1:NDVARGIVKADVAQNNYGLYGQGQVVAVADTGLDTGRNDSSMHEAFRGKITALYALGRTN 60
SD-521  1:NDVARGIVKADVAQNNYGLYGQGQVVAVADTGLDTGRNDSSMHEAFRGKITALYALGRTN 60
A-1     1:NDVARGIVKADVAQSSYGLYGQGQVVAVADTGLDTGRNDSSMHEAFRGKITAIYALGRTN 60
A-2     1:NDVARGIVKADVAQNNFGLYGQGQIVAVADTGLDTGRNDSSMHEAFRGKITALYALGRTN 60
           ************* .******.************************.******

KP43   61:NANDTNGHGTHVAGSVLGNGSTNKGMAPQANLVFQSIMDSGGGLGGLPSNLQTLFSQAYS 120
KP9860 61:NANDTNGHGTHVAGSVLGNGATNKGMAPQANLVFQSIMDSSGGLGGLPSNLQTLFSQAFS 120
KP9865 61:NANDTNGHGTHVAGSVLGNGSTNKGMAPQANLVFQSIMDSGGGLGGLPSNLQTLFSQAYS 120
E-1    61:NANDPNGHGTHVAGSVLGNALNKG-MAPQANLVFQSIMDSSGGLGGLPSNLNTLFSQAWN 119
Ya     61:NASDPNGHGTHVAGSVLGNALNKG-MAPQANLVFQSIMDSSGGLGGLPSNLNTLFSQAWN 119
SD-521 61:NANDPNGHGTHVAGSVLGNALNKG-MAPQANLVFQSIMDSSGGLGGLPSNLNTLFSQAWN 119
A-1    61:NANDPNGHGTHVAGSVLGNGTSNKGMAPQANLVFQSVMDSNGGLGGLPSNVSTLFSQAYS 120
A-2    61:NANDPNGHGTHVAGSVLGNATNK-GMAPQANLVFQSIMDSGGGLGGLPANLQTLFSQAYS 119
          **.*.************         .************.*** *******.*. ******  .

KP43  121:AGARIHTNSWGAAVNGAYTTDSRNVDDYVRKNDMTILFAAGNEGPNGGTISAPGTAKNAI 180
KP9860 121:AGARIHTNSWGAAVNGAYTTDSRNVDDYVRKNDMTILFAAGNEGPNGGTISAPGTAKNAI 180
KP9865 121:AGARIHTNSWGAAVNGAYTTDSRNVDDYVRKNDMTILFAAGNEGPNGGTISAPGTAKNAI 180
E-1   120:AGARIHTNSWGAPVNGAYTANSRQVDEYVRNNDMTVLFAAGNEGPNSGTISAPGTAKNAI 179
Ya    120:AGARIHTNSWGAPVNGAYTANSRQVDEYVRNNDMTVLFAAGNEGPNSGTISAPGTAKNAI 179
SD-521 120:AGARIHTNSWGAPVNGAYTANSRQVDEYVRNNDMTVLFAAGNEGPNSGTISAPGTAKNAI 179
A-1   121:AGARIHTNSWGAPVNGAYTTDSRNVDDYVRKNDMAVLFAAGNEGPNGGTISAPGTAKNAI 180
A-2   120:AGARIHTNSWGAPVNGAYTTDSRNVDDYVRKNDMTILFAAGNEGPGSGTISAPGTAKNAI 179
          ************.******..**.**.***.***. ********:. *************

KP43  181:TVGATENLRPSFGSYADNINHVAQFSSRGPTKDGRIKPDVMAPGTFILSARSSLAPDSSF 240
KP9860 181:TVGATENLRPSFGSYADNINHVAQFSSRGPTKDGRIKPDVMAPGTYILSARSSLAPDSSF 240
KP9865 181:TVGATENLRPSFGSYADNINHVAQFSSRGPTKDGRIKPDVMAPGTFILSARSSLAPDSSF 240
E-1   180:TVGATENYRPSFGSIADNPNHIAQFSSRGATRDGRIKPDVTAPGTFILSARSSLAPDSSF 239
Ya    180:TVGATENYRPSFGSIADNPNHIAQFSSRGATRDGRIKPDVTAPGTFILSARSSLAPDSSF 239
SD-521 180:TVGATENYRPSFGSLADNPNHIAQFSSRGATRDGRIKPDVTAPGTFILSARSSLAPDSSF 239
A-1   181:TVGATENLRPSFGSYADNINHVAQFSSRGPTKDGRIKPDVMAPGTFILSARSSLAPDSSF 240
A-2   180:TVGATENLRPSFGSYADNINHVAQFSSRGPTRDGRIKPDVMAPGTYILSARSSLAPDSSF 239
          *******.******.***.**.*******.*.********.****.************

KP43  241:WANHDSKYAYMGGTSMATPIVAGNVAQLREHFVKNRGITPKPSLLKAALIAGAADIGLGY 300
KP9860 241:WANHDSKYAYMGGTSMATPIVAGNVAQLREHFVKNRGITPKPSLLKAALIAGAADVGLGY 300
KP9865 241:WANHDSKYAYMGGTSMATPIVAGNVAQLREHFVKNRGITPKPSLLKAALIAGAADIGLGY 300
E-1   240:WANYNSKYAYMGGTSMATPIVAGNVAQLREHFIKNRGITPKPSLIKAALIAGATDVGLGY 299
Ya    240:WANYNSKYAYMGGTSMATPIVAGNVAQLREHFIKNRGITPKPSLIKAALIAGATDVGLGY 299
SD-521 240:WANYNSKYAYMGGTSMATPIVAGNVAQLREHFIKNRGITPKPSLIKAALIAGATDVGLGY 299
A-1   241:WANHDSKYAYMGGTSMATPIVAGNVAQLREHFIKNRGITPKPSLLKAALIAGATDIGLGY 300
A-2   240:WANHDSKYAYMGGTSMATPIVAGNVAQLREHFVKNRGVTPKPSLLKAALIAGAADVGLGF 299
          ***..*********************.****.****.*****.******:******.*.***.
```

Fig. 2 b

```
KP43     301:PNGNQGWGRVTLDKSLNVAYVNESSSLSTSQKATYSFTATAGKPLKISLVWSDAPASTTA 360
KP9860   301:PNGNQGWGRVTLDKSLNVAYVNESSALSTSQKATYTFTATAGKPLKISLVWSDAPASTTA 360
KP9865   301:PNGNQGWGRVTLDKSLNVAYVNESSSLSTSQKATYSFTATAGKPLKISLVWSDAPASTTA 360
E-1      300:PSGDQGWGRVTLDKSLNVAYVNEATALTTGQKATYSFQTQAGKPLKISLVWTDAPGSTTA 359
Ya       300:PNGDQGWGRVTLNKSLNVAYVNEATALATGQKATYSFQAQAGKPLKISLVWTDAPGSTTA 359
SD-521   300:PSGDQGWGRVTLDKSLNVAYVNEATALATGQKATYSFQAQAGKPLKISLVWTDAPGSTTA 359
A-1      301:PSGNQGWGRVTLDKSLNVAFVNETSSLSTNQKATYSFTAQSGKPLKISLVWSDAPASTSA 360
A-2      300:PNGNQGWGRVTLDKSLNVAFVNETSPLSTSQKATYSFTAQAGKPLKISLVWSDAPGSTTA 359
            *.*.********.******.***  .*.* *****.*....**********.*** **.*

KP43     361:SVTLVNDLDLVITAPNGTQYVGNDFTSPYNDNWDGRNNVENVFINAPQSGTYTIEVQAYN 420
KP9860   361:SVTLVNDLDLVITAPNGTRYVGNDFSAPFDNNWDGRNNVENVFINSPQSGTYTIEVQAYN 420
KP9865   361:SVTLVNDLDLVITAPNGTQYVGNDFTSPYNNNWDGRNNVENVFINAPQSGTYTIEVQAYN 420
E-1      360:SYTLVNDLDLVITAPNGQKYVGNDFSYPYDNNWDGRNNVENVFINAPQSGTYTIEVQAYN 419
Ya       360:SYTLVNDLDLVITAPNGQKYVGNDFSYPYDNNWDGRNNVENVFINAPQSGTYIIEVQAYN 419
SD-521   360:SYTLVNDLDLVITAPNGQKYVGNDFSYPYDNNWDGRNNVENVFINAPQSGTYTIEVQAYN 419
A-1      361:SVTLVNDLDLVITAPNGTKYVGNDFTAPYDNNWDGRNNVENVFINAPQSGTYTVEVQAYN 420
A-2      360:SLTLVNDLDLVITAPNGTKYVGNDFTAPYDNNWDGRNNVENVFINAPQSGTYTVEVQAYN 419
            * **************..******  *....*****************.******..******

KP43     421:VPVGPQTFSLAIVN                                                434
KP9860   421:VPVGPQNFSLAIVN                                                434
KP9865   421:VPVGPQTFSLAIVN                                                434
E-1      420:VPSGPQRFSLAIVH                                                433
Ya       420:VPSGPQRFSLAIVH                                                433
SD-521   420:VPSGPQRFSLAIVH                                                433
A-1      421:VPQGPQAFSLAIVN                                                434
A-2      420:VPVSPQTFSLAIVH                                                433
            **  .** ******
```

US 7,163,807 B2

NUCLEIC ACID SEQUENCES ENCODING MODIFIED PREPRO PEPTIDES OF AN ALKALINE PROTEASE

CROSS-REFERENCE TO RELATED APPLICATIONS

The present application is a divisional application of U.S. application Ser. No. 10/456,479, filed on Jun. 9, 2003, which issued as U.S. Pat. No. 7,101,698 on Sep. 5, 2006, and which claims priority to JP 2002-186387, filed on Jun. 26, 2002 and JP 2002-304232, filed on Oct. 18, 2002.

TECHNICAL FIELD

The present invention relates to an alkaline protease that is useful as an enzyme to be incorporated into a detergent.

BACKGROUND ART

Among proteases, alkaline proteases to be incorporated into detergents such as laundry detergents are produced in the greatest amounts in the industrial field. Examples of such alkaline proteases known heretofore include Alcalase (registered trademark; Novozymes), Savinase (registered trademark; Novozymes), Maxacal (registered trademark; Genencor), Blap (registered trademark; Henkel), and KAP (Kao Corporation).

Protease is incorporated into a laundry detergent for providing the detergent with the ability to degrade protein soils deposited on clothing. However, actual soils deposited on clothing are complex soils containing, in addition to proteins, a plurality of organic and inorganic components such as sebum-derived lipid, mud, and dust. Therefore, demand has arisen for a detergent exhibiting excellent detergency against such complex soils.

In view of the foregoing, the present inventors have previously found several alkaline proteases having a molecular weight of about 43,000 which maintain sufficient casein-degrading activity even in the presence of fatty acids of high concentrations and which exhibit excellent detergency against complex soils containing proteins and sebum and have previously filed a patent application on the alkaline proteases (see International Publication WO99/18218). These alkaline proteases differ from conventionally known subtilisin, a serine protease derived from bacteria belonging to the genus *Bacillus*, in molecular weight, primary structure, and enzymological characteristics, particularly in having very strong oxidant resistance. Thus, it has been suggested that these alkaline proteases be classified into a new subtilisin subfamily (see Saeki, et al., Biochem. Biophys. Res. Commun., 279, (2000), 313–319).

However, the production amount of such proteases may be insufficient for industrial-scale production, and thus demand has arisen for an alkaline protease which is efficiently produced in a culture medium.

Meanwhile, in order to produce a large amount of the target protein (enzyme), attempts have been made to improve host bacteria (host strains) through mutation breeding, or to modify the gene encoding the enzyme or the gene controlling the expression of the enzyme, thereby enhancing secretion of the enzyme. However, no attempt has been made to enhance secretion of subtilisin by modifying the prepro sequence thereof, which plays an important role in generation and folding.

SUMMARY OF THE INVENTION

Accordingly, the present invention provides an alkaline protease having a prepro sequence, wherein the prepro sequence is a mutated sequence of the amino acid sequence of SEQ ID NO: 1 or an amino acid sequence having 80% or higher homology to the amino acid sequence of SEQ ID NO: 1, in which amino acid residues at (a) position 52, (b) position 75, and (c) position 142 of SEQ ID NO:1, or amino acid residues at positions corresponding to these positions are substituted by the following amino acid residues:

at position (a): aspartic acid or arginine,
  at position (b): alanine or arginine, and
  at position (c): lysine;

and the alkaline protease, when in a mature form, has the amino acid sequence of SEQ ID NO: 2 or an amino acid sequence having a homology of 80% or higher to this amino acid sequence. The present invention also provides a structural gene encoding the alkaline protease; a vector harboring the structural gene; and a transformant comprising the vector.

The present invention also provides a gene encoding the aforementioned mutant prepro sequence.

The present invention also provides a method for producing an alkaline protease having the amino acid sequence of SEQ ID NO: 2, or an amino acid sequence having a homology of 80% or higher to this amino acid sequence, which method comprises employing the aforementioned transformant.

BRIEF DESCRIPTION OF THE DRAWINGS

FIG. 1 shows, in a side-by-side manner of representation, a prepro sequence consisting of the amino acid sequence of SEQ ID NO: 1 and prepro sequences consisting of amino acid sequences having a homology of 80% or higher to this amino acid sequence. In FIG. 1, the order of sequences shown, from top to bottom, are SEQ ID NOs: 1, 8, and 9.

FIGS. 2a and 2b show, in a side-by-side manner of representation, a protease having the amino acid sequence of SEQ ID NO: 2 and proteases having amino acid sequences having a homology of 80% or higher to this amino acid sequence. FIG. 2b is a continuation of FIG. 2a. In FIG. 2, the order of sequences shown, from top to bottom, are SEQ ID NOs: 2 and 10–16.

DETAILED DESCRIPTION OF THE INVENTION

The present inventors have conducted investigations on a novel enzyme which maintains the aforementioned characteristics of the alkaline protease and is efficiently produced in a culture medium, and have found that, when an amino acid residue at a specific position of the prepro sequence of the alkaline protease is replaced with a specific amino acid residue, productivity of the alkaline protease can be enhanced.

The prepro sequence of the alkaline protease of the present invention (which may be referred to as "mutant prepro sequence") is a modified (or mutated) sequence of the amino acid sequence of SEQ ID NO: 1 or an amino acid sequence having 80% or higher homology to the amino acid sequence of SEQ ID NO: 1, in which amino acid residues at position 52 (may be referred to as position (a)), position 75 (may be referred to as position (b)), and position 142 (may be referred to as position (c)) of SEQ ID NO:1 or amino acid residues at positions corresponding to these positions are substituted by the following amino acid residues:
at position (a): aspartic acid or arginine,
at position (b): alanine or arginine, and
at position (c): lysine.

In the present invention, the prepro sequence may be a wild-type mutant sequence or an artificially mutated sequence.

The prepro sequence is a critical region relating to secretion and folding of the alkaline protease. The pre-sequence is a signal sequence, and is cleaved by signal peptidase when an alkaline protease precursor passes through a cell membrane. Meanwhile, the pro-sequence is known to act as an intramolecular chaperonin, and is an essential region for providing the alkaline protease with a correct three-dimensional structure before and after it passes through a cell membrane. The pro-sequence is finally cleaved by mature alkaline protease, and is degraded into small peptides. A product obtained through transcription and translation of the structural gene encoding the alkaline protease is present in a cell in the form of an alkaline protease precursor having a prepro sequence. Therefore, the alkaline protease having a prepro sequence of the present invention refers to an alkaline protease precursor.

Examples of the amino acid sequence of SEQ ID NO: 1; i.e., a non-mutated prepro sequence, include the prepro sequence of KP43 [derived from *Bacillus* sp. KSM-KP43 (FERM BP-6532), International Publication WO99/18218].

Among amino acid sequences having a homology of 80% or higher to the amino acid sequence of SEQ ID NO: 1, preferred are those having a homology of 87% or higher, more preferably 90% or higher, still more preferably 95% or higher, even still more preferably 98% or higher. Amino acid sequences having 80% or higher homology to the amino acid sequence of SEQ ID NO: 1 are preferably prepro sequences of an alkaline protease consisting of an amino acid sequence having a homology of 80% or higher to the amino acid sequence of SEQ ID NO:2 described below. Specific examples of such an amino acid sequence include the prepro sequence of protease KP9860 (GenBank Accession No. AB046403) [derived from *Bacillus* sp. KSM-KP9860 (FERM BP-6534), International Publication WO99/18218], and the prepro sequence of protease 9865 (GenBank Accession No. AB084155) [derived from *Bacillus* sp. KSM-9865 (FERM P-18566), Japanese Patent Application No. 2002-2653]. The homologies of the prepro sequences of protease KP9860 and protease 9865 to the amino acid sequence of SEQ ID NO: 1 are 86.8% and 97.6%, respectively (FIG. 1).

The homology between amino acid sequences is calculated by means of programs such as GENETYX WIN maximum matching or search homology (products of Software Development Co., Ltd.).

"Amino acid residues at positions corresponding to these positions" can be identified by comparing amino acid sequences of alkaline proteases by means of a known algorithm such as the Lipman-Person method, to thereby assign maximum homology to conserved amino acid residues present in the amino acid sequence of each alkaline protease. When the amino acid sequences of the prepro sequences are aligned by means of such a method, the positions of the homologous amino acid residues in each of the prepro sequences can be determined regardless of insertion or deletion of amino acid residue(s) in the amino acid sequences. Conceivably, the homologous amino acid residues are located at the same positions in the three-dimensional structures of the prepro sequences, and thus the alkaline proteases having the prepro sequences are analogous in terms of specificity-related functions.

As shown in FIG. 1, in which amino acid sequences are aligned by means of the aforementioned method, the amino acid residues at (a) position 52, (b) position 75, and (c) position 142 of SEQ ID NO: 1 are lysine, glutamine, and glutamic acid, respectively. The amino acid residues at positions corresponding to positions (a) through (c) can be identified by means of the aforementioned method. For example, in the prepro sequence of protease KP9860 or protease 9865, the amino acid residues at (a) position 52, (b) position 75, and (c) position 142 are lysine, glutamine, and glutamic acid, respectively.

In the mutant prepro sequence of the alkaline protease of the present invention, the amino acid residue at (a) position 52 of SEQ ID NO: 1 or at a position corresponding to this position is preferably substituted by aspartic acid or arginine, particularly preferably by arginine. The amino acid residue at (b) position 75 or at a position corresponding to this position is preferably substituted by alanine or arginine, particularly preferably by arginine. The amino acid residue at (c) position 142 or at a position corresponding to this position is particularly preferably substituted by lysine.

In the mutant prepro sequence of the alkaline protease of the present invention, substitution of amino acid residues may be performed at two or more positions selected from positions (a) through (c), so long as characteristics of the resultant enzyme do not vary. Specific examples of combinations of substitution of amino acid residues at two or more positions include Lys52(Asp/Arg)+Gln75(Ala/Arg), Lys52(Asp/Arg)+Glu142Lys, Lys52(Asp/Arg)+Glu142Lys, and Gln75(Ala/Arg)+Lys52(Asp/Arg)+Glu142Lys. Preferred combinations are Lys52 Arg+Gln75Arg, Lys52Asp+Gln75Ala, and Lys52Asp+Glu142Lys. The combination Lys52Arg+Glu142Lys is particularly preferred. Amino acids are designated by the three letters; the symbol "+" refers to the case where additional substitution is performed; and the symbol "/" refers to the case where either of the right and left two amino acids may be employed for substitution.

The alkaline protease of the present invention has the aforementioned mutant prepro sequence, and the alkaline protease, when in a mature form, has the amino acid sequence of SEQ ID NO: 2 or an amino acid sequence having a homology of 80% or higher to this amino acid sequence.

As the amino acid sequences having 80% or higher homology to the amino acid sequence of SEQ ID NO: 2, preferred are those having a homology of 87% or higher, more preferably 90% or higher, still more preferably 95% or higher, and even still more preferably 98% or higher. Such alkaline protease may be a wild-type alkaline protease or a variant. Preferably, the alkaline protease exhibits oxidant resistance, and has a molecular weight of 43,000±2,000 as determined by sodium dodecyl sulfate polyacrylamide gel electrophoresis (SDS-PAGE). Preferably, the alkaline protease has the following characteristics: acting within an alkaline region at a pH of 8 or higher, exhibiting oxidant resistance, its enzymatic activity being not inhibited in the presence of a fatty acid of high concentration, exhibiting high gelatin-degrading activity, exhibiting at least 80% residual activity when treated at 50° C. and a pH of 10 for 10 minutes, being inhibited by diisopropyl fluorophosphate (DFP) and phenylmethanesulfonyl fluoride (PMSF), and having a molecular weight of 43,000±2,000 as determined by SDS-PAGE.

As used herein, the expression "the alkaline protease exhibits oxidant resistance" refers to the case where, after the alkaline protease is allowed to stand at 30° C. for 20 minutes in a 20 mM Britton-Robinson buffer (pH 10) containing hydrogen peroxide (50 mM) and calcium chloride (5 mM), the alkaline protease maintains at least 50% residual activity. So long as the alkaline protease maintains the aforementioned characteristics, the alkaline protease may be a wild-type, variant, or artificially mutated alkaline protease.

Examples of the alkaline protease having the amino acid sequence of SEQ ID NO: 2 (mature alkaline protease) include KP43 [derived from *Bacillus* sp. KSM-KP43 (FERM BP-6532), International Publication WO99/18218]. Examples of the alkaline protease having an amino acid sequence having a homology of 80% or higher to the amino acid sequence of SEQ ID NO: 2 include protease KP9860 (GenBank Accession No. AB046403) [derived from *Bacillus* sp. KSM-KP9860 (FERM BP-6534), International Publication WO99/18218]; protease 9865 (GenBank Accession No. AB084155) [derived from *Bacillus* sp. KSM-9865 (FERM P-1592), Japanese Patent Application No. 2002-002653]; protease E-1 (GenBank Accession No. AB046402) [derived from *Bacillus* No. D-6 (FERM P-1592), Japanese Patent Application Laid-Open (kokai) No. 49-71191]; protease Ya (GenBank Accession No. AB046404) [derived from *Bacillus* sp. Y (FERM BP-1029), Japanese Patent Application Laid-Open (kokai) No. 61-280268]; protease SD521 (GenBank Accession No. AB046405) [derived from *Bacillus* SD521 (FERM P-11162), Japanese Patent Application Laid-Open (kokai) No. 3-191781]; protease A-1 (GenBank Accession No. AB046406) [derived from NCIB12289, International Publication WO88/01293]; protease A-2 [derived from NCIB12513, International Publication WO98/56927]; a mutant obtained through substitution at position 46 of the amino acid sequence of SEQ ID NO: 2 by leucine; a mutant obtained through substitution at position 57 by alanine; a mutant obtained through substitution at position 103 by arginine; a mutant obtained through substitution at position 107 by lysine; a mutant obtained through substitution at position 124 by lysine or alanine; a mutant obtained through substitution at position 136 by alanine; a mutant obtained through substitution at position 193 by alanine; a mutant obtained through substitution at position 195 by asparagine, glutamic acid, arginine, proline, threonine, valine, histidine, serine, lysine, glutamine, methionine, cysteine, alanine, aspartic acid, tryptophan, glycine, or phenylalanine; a mutant obtained through substitution at position 247 by threonine or arginine; a mutant obtained through substitution at position 257 by valine; a mutant obtained through substitution at position 342 by alanine; a double-mutant obtained through substitution at positions 66 and 264 by aspartic acid and serine, respectively (Japanese Patent Application No. 2000-355166 (Japanese Patent Application Laid-Open (kokai) No. 2002-218989)); a mutant obtained through substitution at position 84 of the amino acid sequence of SEQ ID NO: 2 by arginine; a mutant obtained through substitution at position 104 by proline; a mutant obtained through substitution at position 256 by alanine or serine; a mutant obtained through substitution at position 369 by asparagine (Japanese Patent Application Laid-Open (kokai) No. 2002-306176); a mutant obtained through substitution at position 251 of the amino acid sequence of SEQ ID NO: 2 by asparagine, threonine, isoleucine, valine, leucine, or glutamine; a mutant obtained through substitution at position 256 by serine, glutamine, asparagine, valine, or alanine (Japanese Patent Application No. 2001-329472); and an alkaline protease having an amino acid sequence having a homology of 80% or higher, preferably 87% or higher, more preferably 90% or higher, still more preferably 95% or higher, to the amino acid sequences of the aforementioned proteases. FIGS. 2a and 2b show, in a side-by-side manner of representation, the amino acid sequences of some of the aforementioned alkaline proteases.

Cloning of the gene encoding the alkaline protease of the present invention may be performed by means of shotgun cloning, PCR, or the like. The thus-cloned gene may be subjected to mutagenesis. An example of the base sequence of the thus-obtained gene is shown as SEQ ID NO: 3. The gene encoding the prepro sequence of SEQ ID NO: 1 or a prepro sequence having a homology of 80% or higher to this prepro sequence may be cloned by means of PCR or the like.

Mutagenesis of the gene encoding the prepro sequence may be performed by means of random mutagenesis or site-directed mutagenesis, which is a customary technique. More specifically, mutagenesis of the gene may be performed by use of, for example, a Site-Directed Mutagenesis System Mutan-Super Express Km kit (Takara).

The method for producing the protease of the present invention by use of the thus-obtained mutant prepro gene will now be described. When the gene encoding the prepro sequence of the alkaline protease—the base sequence of the gene is shown in SEQ ID No: 3—is mutated, the resultant mutant gene is employed as is. Meanwhile, when the gene encoding a mature enzyme having an amino acid sequence having a homology of 80% or higher to the amino acid sequence of SEQ ID NO: 2 is ligated to the downstream region of the mutant prepro gene, a structural gene may be produced by providing an appropriate restriction enzyme cleavage site by means of site-directed mutagenesis or by employing recombinant PCR or the like. Subsequently, the mutant gene is introduced into a plasmid vector, and a host bacterium which can reliably amplify and maintain the vector is transformed. Alternatively, the mutant gene is introduced into chromosomal DNA of a host bacterium which can reliably maintain the gene. Examples of the host bacterium which satisfies the aforementioned requirements include bacteria belonging to the genus *Bacillus, Escherichia coli*, mold, yeast, and actinomycetes. The host bacterium containing the mutant gene is inoculated into a culture medium containing an assimilable carbon source, nitrogen source, and other essential nutrients, and cultured according to the customary method.

Thus, the alkaline protease having a prepro sequence of the present invention, which is expressed in the host cells, is effectively produced by the transformants.

As used herein, the expression "effectively produced" refers to the case where, when a mutant alkaline protease is produced under the same conditions as those employed for production of a non-mutated alkaline protease (for example, inoculation into a culture medium containing polypeptone S (8% (w/v)), yeast extract (0.3%), maltose (10%), magnesium sulfate heptahydrate (0.04%), potassium dihydrogenphosphate (0.2%), sodium carbonate anhydrate (1.5%), and tetracycline (30 ppm); and shaking the culture at 30° C. for three days), and the activity and the amount of protein in the culture supernatant are measured, the activity or amount of the protease is at a certain level or higher. For example, the expression "effectively produced" refers to the case where the activity or the amount of protein is increased by at least 5%, preferably at least 10%, more preferably at least 15% compared with that of parental alkaline protease. When variation in, for example, specific activity of the thus-produced alkaline protease is not confirmed, either the activity or amount of the protease may be measured.

The prepro sequence is cleaved out of the alkaline protease, and a mature enzyme is secreted outside the host cells. The mature enzyme may be collected and purified by means of usual methods for collecting and purifying enzymes. For example, the culture broth is subjected to centrifugation or filtration, to thereby remove the host cells, and the aimed enzyme is obtained from the culture supernatant by means of a customary purification technique. The thus-obtained enzyme solution may be employed without any treatment. Alternatively, the enzyme solution may be additionally subjected to purification, crystallization, powdering, or granulation by means of a known method.

The thus-obtained alkaline protease exhibits oxidant resistance, maintains casein-degrading activity even in the presence of a fatty acid of high concentration, and exhibits high gelatin-degrading activity. In addition, the alkaline protease preferably has a molecular weight of 43,000±2,000 as determined by SDS-PAGE, and beneficially exhibits activity within the alkaline region. Therefore, the alkaline protease can be employed in, for example, laundry detergents, bleaching agents, detergents for cleaning hard surfaces, detergents for drainpipes, denture-cleaning agents, and detergents for sterilizing medical apparatuses.

EXAMPLES

Example 1

A DNA fragment of about 2.0 kb (including a termination codon) of the alkaline protease structural gene (SEQ ID NO: 3) derived from *Bacillus* sp. strain KSM-KP43 was subjected to random mutagenesis. Firstly, PCR was performed by use of BcaBEST Sequencing Primer RV-M (Takara) and BcaBEST Sequencing Primer M13-47 (Takara) which can amplify the aforementioned DNA of about 2.0 kb introduced into the multi-cloning site of pKF18k (Takara). The reaction was performed by the use of the template DNA (30 ng), each primer (20 pmol), each dNTP (20 nmol), appropriate amounts of manganese sulfate and dimethyl sulfoxide, Takara Taq-added reaction buffer (10 µL), and Taq polymerase (2.5 U) (total amount of these substances: 100 µL). The PCR was performed for 30 cycles, each cycle including 94° C.×one minute, 55° C.×two minutes, and 72° C.×three minutes, and the resultant PCR product was maintained at 72° C. for 10 minutes. The PCR product was purified by use of a High Pure PCR Product Purification kit (Roche), and eluted with sterile water (100 µL). The thus-obtained DNA fragment of about 2.0 kb was cleaved by BamHI and XbaI (Roche), and then mixed with pKF18k which had been treated with these enzymes, to thereby perform ligation by use of a DNA Ligation kit ver. 2 (Takara). *Escherichia coli* HB101 cells were transformed by use of the resultant reaction mixture, and grown on an LB agar medium containing kanamycin (100 µg/mL). The thus-obtained transformant was inoculated into an LB medium containing kanamycin (100 µg/mL), and subjected to shaking culture at 30° C. The activity of the resultant culture supernatant was measured by use of a synthetic substrate (Glt-Ala-Ala-Pro-Leu-pNA, Peptide Institute); a culture broth having an activity higher than that of the parental alkaline protease was selected; and PCR was performed under the same conditions as described above by use of a small amount of the strain, BcaBEST Sequencing Primer RV-M, and BcaBEST Sequencing Primer M13-47, to thereby amplify mutant genes. The thus-amplified gene fragments were purified, and the nucleotide sequence of each of the fragments was determined by use of a DNA Sequencer (model: 377, Applied Biosystems) employing an appropriate primer and a Big Dye DNA sequencing kit (Applied Biosystems).

As a result, a mutant exhibiting enhanced protease activity was found to be produced by expression of each of the mutant genes in which lysine at position 52, glutamine at position 75, and glutamic acid at position 142 of the amino acid sequence of SEQ ID NO: 1 were substituted by arginine, arginine, and lysine, respectively, and the protease activity of the mutant was found to be increased by 2 to 10%. Subsequently, the alkaline protease structural gene was subjected to mutation in order to confirm the effects of substitution of the amino acids at the above mutation positions by other amino acids. For mutagenesis, the amino acids at positions 52, 75, and 142 were substituted by arbitrary amino acids by use of a Site-Directed Mutagenesis System Mutan-Super Express Km kit (Takara). PCR was performed by the use of template plasmid (plasmid obtained through introduction of the protease structural gene into BamHI and XbaI sites of pKF18k) (30 ng), a selection primer attached to the kit, primers Nos. 3 through 5 (SEQ ID NOs: 5 through 7) (20 pmol for each), and Takara LA Taq. The reaction was performed for 30 cycles, each cycle including 94° C.×one minute, 55° C.×two minutes, and 72° C.×three minutes. The resultant PCR fragment was purified. Additionally, PCR was performed by use of the purified fragment serving as a primer, template plasmid (30 ng), and LA Taq. The reaction was performed for 30 cycles, each cycle including 94° C.×one minute, 55° C.×two minutes, and 72° C.×four minutes. The resultant PCR product was purified and subjected to ligation. Thereafter, *Escherichia coli* MV1184 strain was transformed by use of the PCR product. Plasmid DNA is extracted from the transformed strain, and *Escherichia coli* HB101 cells were transformed by use of the plasmid DNA. The transformant was inoculated into an LB medium containing kanamycin (100 µg/mL), and subjected to shaking culture at 30° C. The activity of the resultant culture supernatant was measured by use of a synthetic substrate, and a culture broth having an activity higher than that of the parental alkaline protease was selected. PCR was performed by use of the strain serving as a template, to thereby amplify mutant genes, and the amplified genes were purified. After purification, the nucleotide sequence of each of the genes was determined. As a result, the activities of the mutant in which lysine at position 52 was substituted by aspartic acid and the mutant in which glutamine at position 75 was substituted by alanine were found to be higher than that of the parental alkaline protease by 5% and 10%, respectively. A mutant in which the amino acid at position 142 was substituted by an amino acid other than lysine failed to exhibit enhanced protease activity.

Furthermore, the effect of combinations of the aforementioned mutation positions on enhancement of protease activity was investigated. A BamHI-XhoI fragment in which the amino acid at position 52 was mutated, an XhoI-AatII fragment in which the amino acid at position 142 was mutated, and an AatII-XbaI fragment containing the gene encoding a mature enzyme were prepared, and these fragments were mixed with pKF18k which had been treated with BamHI and XbaI, to thereby perform ligation. An *Escherichia coli* HB101 cells were transformed by the use of the resultant plasmid DNA, and a double-mutant containing the mutation Lys52Arg and the mutation Glu142Lys was produced through culture. As a result, the activity of the Lys52Arg+Glu142 Lys mutant was found to be higher than that of the Lys52Arg mutant by 10%.

Example 2

When KP43 protease was employed as the parental alkaline protease, each of the above-obtained mutant prepro sequences was found to have the effect of enhancing activity of the resultant mutant as described above. Further investigations were performed for confirming the effect of the prepro sequence of the present invention on the mutant alkaline protease exhibiting enhanced secretion and specific activity (alkaline protease KP43H obtained through the following substitution of the amino acid sequence of SEQ ID NO: 2:

Phe46Leu/Thr65Pro/Tyr195Gly/Val273Ile/Thr359Ser/

Asp369Asn/Ser387Ala).

The gene fragment encoding each of the mutant prepro sequences was cleaved out of pKF18k by the use of BamHI and AatII, and, by the use of ligase, the gene fragment was ligated to the gene encoding KP43H, which was cleaved out of pKF18k by the use of AatII and XbaI (the AatII site was newly produced through site-specific substitution of a nucleotide without changing the amino acid encoded by the gene). *Escherichia coli* HB101 cells were transformed by the use of the resultant plasmids. After being extracted, each of the plasmids was cleaved by the use of BamHI and XbaI. The resultant fragments were introduced into pHA64 which had previously been treated with these enzymes, and *Bacillus* sp. strain KSM-KP43 were transformed by means of electroporation employing SSH-10 (Shimadzu Corporation) and gene pulser cuvette (Bio-Rad). Introduction of the protease gene was determined on the basis of the generation of skim milk dissolution spots of transformants formed on a skim milk-containing alkaline agar medium [skim milk (Difco) (1% (w/v)), bactotryptone (Difco) (1%), yeast extract (Difco) (0.5%), sodium chloride (0.5%), agar (1.5%), sodium carbonate anhydrate (0.05%), and tetracycline (15 ppm)]. Transformants containing plasmids in which the protease gene was inserted into pHA64 were selected, and the strains were subjected to the below-described culture.

Single colony isolation and halo formation were confirmed in each of the transformants, and the strain was inoculated into a seed culture medium (5 mL) [polypeptone S (Nihon Pharmaceutical Co., Ltd.) (6.0% (w/v)), yeast extract (0.1%), maltose (1.0%), magnesium sulfate heptahydrate (0.02%), potassium dihydrogenphosphate (0.1%), sodium carbonate anhydrate (0.3%), and tetracycline (30 ppm)] in a test tube, followed by pre-culture at 30° C. and 320 rpm overnight. The resultant seed culture broth (1% (v/v)) was inoculated into a culture medium (20 mL) [polypeptone S (8% (w/v)), yeast extract (0.3%), maltose (10%), magnesium sulfate heptahydrate (0.04%), potassium dihydrogenphosphate (0.2%), sodium carbonate anhydrate (1.5%), and tetracycline (30 ppm)] in a Sakaguchi flask (capacity: 500 mL), followed by culture at 30° C. and 121 rpm for three days. The resultant culture broth was subjected to centrifugation, and the protease activity of the resultant culture supernatant was measured. The protease activity was measured by means of the casein method, and the amount of the resultant protein was measured by the use of a protein assay kit (Wako Pure Chemical Industries, Ltd.). As a result, the activity of the alkaline protease KP43H having the mutant prepro sequence was found to be increased by 5 to 25% compared with that of the control (a product produced through culture of a transformant having an alkaline protease KP43H gene under the aforementioned conditions) (Table 1). Plasmids were collected from the above-selected transformants, and the base sequence of each of the plasmids was determined. As a result, it was confirmed that the transformants were aimed mutant.

It was found that the alkaline protease produced by the use of the aforementioned mutant prepro sequence was produced in the transformant in an increased amount. In addition, it was also found that the alkaline protease exhibits the characteristics of the parental alkaline protease; specifically, exhibiting oxidant resistance, exhibiting high gelatin-degrading activity, its casein-degrading activity being not inhibited by a fatty acid of high concentration, having a molecular weight of 43,000±2,000 as determined by SDS-PAGE, and exhibiting activity within an alkaline region.

[Protease Assay—Synthetic Substrate Method]

A synthetic substrate (Glt-Ala-Ala-Pro-Leu-pNA: AAPL) was employed for the measurement of enzymatic activity. A solution containing a 100 mM borate buffer (pH 10.5) (48.5 µL) and 100 mM AAPL (1.5 µL) was added to a 96-well assay plate (Iwaki), and an appropriately diluted enzyme solution or culture broth (50 µL) was added thereto, to thereby initiate reaction at 30° C. for 15 minutes by the use of an iEMS Reader MS (LABSYSTEMS). The absorbance of liberated p-nitroaniline was measured at 414 nm. One unit of enzymatic activity was defined as the amount of the enzyme required for increasing the absorbance by 0.001 per minute under the above reaction conditions.

[Protease Assay—Casein Method]

A 50 mM borate buffer (pH 10.5) (1.0 mL) containing casein (1% (w/v)) was maintained at 30° C. for five minutes, and subsequently an enzyme solution (0.1 mL) was added to the buffer, to thereby allow reaction to proceed for 15 minutes. A reaction stopping solution (0.11 M trichloroacetic acid-0.22 M sodium acetate-0.33 M acetic acid) (2.0 mL) was added to the resultant reaction mixture, and the mixture was allowed to stand at room temperature for 30 minutes. Thereafter, the resultant mixture was subjected to filtration, and the amount of an acid-soluble protein in the resultant filtrate was measured by means of a modification of the method of Lowry, et al. Specifically, an alkaline copper solution (1% potassium sodium tartrate:1% copper sulfate pentahydrate:2% sodium carbonate-0.1 N sodium hydroxide=1:1:100) (2.5 mL) was added to the filtrate (0.5 mL), and the resultant mixture was allowed to stand at room temperature for 10 minutes. Subsequently, to the mixture was added a phenol solution [obtained by diluting a phenol reagent (Kanto Kagaku) two-fold with distilled water] (0.25 mL), and the resultant mixture was incubated at 30° C. for 30 minutes. Thereafter, the absorbance of the mixture was measured at 660 nm. One unit of protease activity (1 PU) was defined as the amount of the enzyme required for liberating acid-soluble protein degradation products equivalent to 1 mmol of tyrosine per minute under the above reaction conditions.

TABLE 1

| Mutant | Relative activity (%) |
| --- | --- |
| KP43H (control) | 100 |
| Lys52Asp | 105 |
| Lys52Arg | 119 |
| Gln75Ala | 110 |
| Gln75Arg | 110 |
| Glu142Lys | 107 |
| Lys52Arg/Glu142Lys | 125 |

Example 3

(1) Preparation of Detergent

Water (465 kg) was added to a mixing tank (1 m$^3$) equipped with a stirring paddle. After the temperature of the water reached 55° C., a 40% (w/v) aqueous solution of sodium polyacrylate (135 kg) was added to the water. After the resultant mixture was stirred for 15 minutes, sodium carbonate (120 kg), sodium sulfate (60 kg), sodium sulfite (9 kg), and a fluorescent dye (3 kg) were added to the mixture. After the resultant mixture was stirred for additional 15 minutes, zeolite (300 kg) was added to the mixture, and then stirred for 30 minutes, to thereby yield a homogenous slurry (the water content of the slurry: 50 mass %). The slurry was sprayed through a pressure spray nozzle provided in the vicinity of the top of a spray-drying tower, to thereby yield a granular base (a high-temperature gas was fed at 225° C. through a lower part of the spray-drying tower, and discharged at 105° C. from the top of the tower).

Subsequently, the thus-obtained granular base (100 parts by mass) was fed to a Lodige mixer (product of Matsuzaka Giken Co., Ltd., capacity: 20 L, equipped with a jacket). While the granular base was stirred with the main shaft (150 rpm), a mixture of a nonionic surfactant (20 parts by mass), sodium linear alkyl (C10–C13) benzenesulfonate (22 parts by mass), a sodium salt of a fatty acid (C14–C18)(4 parts by mass), polyethylene glycol (2 parts by mass), and water (4 parts by mass) was added to the mixer over three minutes. Thereafter, the resultant mixture was stirred for five minutes. Furthermore, crystalline sodium silicate (20 parts by mass) and zeolite (10 parts by mass) were added to the mixer, to thereby perform surface coating and yield a detergent base.

The detergent base (99 mass %) was mixed with granules of the protease of the present invention (0.5 mass %) and a perfume (0.5 mass %), to thereby produce final granular detergent A.

(2) Raw Materials Employed

Nonionic surfactant: Emulgen 108 KM (average molar number of ethylene oxide added: 8.5, product of Kao Corporation)

Aqueous solution of sodium polyacrylate: average molecular weight: 10,000 (produced according to the method described in Examples of Japanese Patent Publication (kokoku) No. 2-24283)

Sodium carbonate: Dense ash (product of Central Glass Co., Ltd.)

Zeolite: Zeolite 4A (average particle size: 3.5 µm, product of Tosoh Corporation)

Polyethylene glycol: K-PEG6000 (average molecular weight: 8,500, product of Kao Corporation)

Crystalline sodium silicate: Powder SKS-6 (product of Hoechst Tokuyama Co., Ltd.)

Granules of the protease of embodiments of the present invention: granules (6 PU/g) prepared from each of the purified samples of the alkaline protease of embodiments of the present invention shown in Table 1 by use of the method described in Example 1 of Japanese Patent Application Laid-Open (kokai) No. 62-257990

Fluorescent dye: Tinopal CBS-X (product of Ciba-Geigy Corp.)

Example 4

(1) Preparation of Detergent

The slurry (solid content: 50 mass %) was spray-dried with hot air at 250° C., to thereby yield a granular base containing sodium polyacrylate (mass average molecular weight: 10,000) (7 mass %), sodium carbonate (26 mass %), sodium sulfate (20 mass %), sodium chloride (6 mass %), the fluorescent dye (0.5 mass %), zeolite (40 mass %), and water (0.5 mass %).

Subsequently, the thus-obtained granular base (100 parts by mass) was fed to a Lodige mixer (product of Matsuzaka Giken Co., Ltd., capacity: 20 L, equipped with a jacket). While the granular base was stirred with the main shaft (150 rpm), a mixture of a nonionic surfactant (20 parts by mass), sodium linear alkyl (C10–C13) benzenesulfonate (22 parts by mass), a sodium salt of a fatty acid (C14–C18)(4 parts by mass), polyethylene glycol (2 parts by mass), and water (4 parts by mass) was added to the mixer over three minutes. Thereafter, the resultant mixture was stirred for five minutes. Furthermore, crystalline sodium silicate (20 parts by mass) and zeolite (10 parts by mass) were added to the mixer, to thereby perform surface coating and yield a detergent base.

The detergent base (95 mass %) was mixed with bleaching agent granules (2.8 mass %), bleaching activator granules (1.2 mass %), granules of the protease of embodiments of the present invention (0.5 mass %) and a perfume (0.5 mass %), to thereby produce final granular detergent B.

(2) Raw Materials Employed

Nonionic surfactant: Emulgen 108 KM (average mole number of ethylene oxide added: 8.5, product of Kao Corporation)

Aqueous solution of sodium polyacrylate: average molecular weight: 10,000 (produced according to the method described in Examples of Japanese Patent Publication (kokoku) No. 2-24283)

Sodium carbonate: Dense ash (product of Central Glass Co., Ltd.)

Zeolite: Zeolite 4A (average particle size: 3.5 µm, product of Tosoh Corporation)

Polyethylene glycol: K-PEG6000 (average molecular weight: 8,500, product of Kao Corporation)

Crystalline sodium silicate: SKS-6 (product of Hoechst Tokuyama Co., Ltd.)

Granules of the protease of embodiments of the present invention: granules (6 PU/g) prepared from each of the purified samples of the alkaline protease of embodiments of the present invention shown in Table 1 according to the method described in Example 1 of Japanese Patent Application Laid-Open (kokai) No. 62-257990

Fluorescent dye: Tinopal CBS-X (product of Ciba-Geigy Corp.)

Bleaching agent granules: a sodium carbonate-hydrogen peroxide addition product (produced in a manner similar to that for producing bleaching agent granules described in paragraph [0019] of Japanese Patent Application Laid-Open (kokai) No. 2000-256699)

Bleaching activator granules: granules of sodium lauroyloxybenzenesulfonate (produced in a manner similar to that for producing bleaching activator granules described in paragraph [0018] of Japanese Patent Application Laid-Open (kokai) No. 2000-256699)

Example 5

Liquid detergent compositions (detergents C and D) shown in Table 2 were prepared.

TABLE 2

| Components | Detergent C (mass %) | Detergent D (mass %) |
|---|---|---|
| Nonionic surfactant[1] | 25.0 | — |
| Nonionic surfactant[2] | 5.0 | — |
| Nonionic surfactant[3] | 10.0 | — |
| Nonionic surfactant[4] | — | 9.0 |
| Nonionic surfactant[5] | — | 9.0 |
| Nonionic surfactant[6] | — | 2.5 |
| Anionic surfactant[7] | 1.0 | — |
| Silicone[8] | — | 0.8 |
| Carboxylic acid-based polymer[9] | 2.0 | — |
| Polymer[10] | — | 0.8 |
| Citric acid | 0.2 | — |
| Calcium chloride | 0.05 | — |
| Monoethanolamine | 4.0 | — |
| Triethylene glycol phenyl ether | 3.0 | — |
| Propylene glycol | 3.0 | — |
| Ethanol | 2.0 | 2.0 |
| Sodium sulfite | 0.2 | — |
| Protease[11] | 0.5 | 1.0 |
| Perfume | 0.5 | 0.5 |
| Water | Balance | Balance |
| Total | 100 | 100 |
| Concentration upon use | 20 g/30 L | 40 g/30 L |
| pH of liquid detergent | 10.5 | 7.3 |

[1] Polyoxyethylene (average molar number of EO added: 7) alkyl ether having an alkyl group derived from a C12–C14 secondary alcohol (Softanol 70, product of Nippon Shokubai Co., Ltd.)
[2] Polyoxyethylene (average molar number of EO added: 12) alkyl ether having an alkyl group derived from a C12–C14 secondary alcohol (Softanol 120, product of Nippon Shokubai Co., Ltd.)
[3] A product obtained by subsequently adding EO (average molar number: 5), PO (average molar number: 2), and EO (average molar number: 3) to a C10–C14 linear primary alcohol
[4] Polyoxyethylene lauryl ether (average molar number of EO added: 8)
[5] Polyoxyethylene lauryl ether (average molar number of EO added: 11.5)
[6] Narrow range polyoxyethylene alkyl (sec-$C_{12}/C_{13}$) ether
[7] Sodium linear alkyl (C10–C14) benzenesulfonate
[8] Amide/ether-modified silicone polymer (BY16-906, product of Dow Corning Toray Silicone Co., Ltd.)
[9] A phenoxypolyethylene glycol - acrylic acid - maleic acid copolymer synthesized according to the method described in lines 6 through 13 of page 11 of Japanese Patent Application Laid-Open (kokai) No. 10-60476 (mass average molecular weight: 10,000, solid content: 51.2%)
[10] A sodium salt of a pentene/maleic acid (molar ratio: 50/50) copolymer (mass average molecular weight: 7,000)
[11] Each of the purified samples of the alkaline protease of embodiments of the present invention shown in Table 1 (15 PU/g)

Example 6

While sodium percarbonate and sodium carbonate (dense ash) of the components shown in the below-described Table 3 were mixed under stirring, a 40% aqueous solution of sodium polyacrylate, sodium linear alkyl benzenesulfonate or a nonionic surfactant, and sodium lauroyloxybenzenesulfonate were added to the mixture. Subsequently, to the resultant mixture was added granules of the protease of an embodiment of the present invention prepared according to the method described in Example 1 of Japanese Patent Application Laid-Open (kokai) No. 62-257990, and the resultant mixture was stirred so as to attain uniformity in the entirety of the mixture, thereby preparing a bleaching agent.

TABLE 3

| Components | Bleaching agent E (mass %) | Bleaching agent F (mass %) |
|---|---|---|
| Sodium percarbonate[1] | 72.0 | 72.0 |
| Sodium carbonate (dense ash) | 20.0 | 20.0 |
| Anionic surfactant[2] | 2.0 | — |
| Nonionic surfactant[3] | — | 2.0 |
| Sodium polyacrylate[4] | 1.0 | 1.0 |
| Sodium lauroyloxybenzenesulfonate | 4.0 | 4.0 |
| Protease[5] | 1.0 | 1.0 |

[1] Particle size: 500 to 700 μm
[2] Sodium linear alkyl (C12–C14) benzenesulfonate
[3] Polyoxyethylene alkyl ether (number of carbon atoms of the alkyl group: 12 to 14, average molar number of EO added: 12)
[4] Average molecular weight: 8,000
[5] Granules (6 PU/g) prepared from each of the purified samples of the alkaline protease of an embodiment of the present invention shown in Table 1 according to the method described in Example 1 of Japanese Patent Application Laid-Open (kokai) No. 62-257990

Example 7

Detergent compositions for an automatic dishwasher (detergents G and H) shown in the below-described Table 4 were prepared.

TABLE 4

| Components | Detergent G (mass %) | Detergent H (mass %) |
|---|---|---|
| Pluronic L-61[1] | — | 4.0 |
| Softanol EP-7085[2] | 4.0 | — |
| Trisodium citrate | — | 30.0 |
| Sodium tripolyphosphate | 30.0 | — |
| Sodium percarbonate | 20.0 | 20.0 |
| Sodium carbonate | 20.0 | 20.0 |
| Amorphous silicate[3] | 10.0 | 10.0 |
| AA-MA[4] | 4.0 | 4.0 |
| Sodium sulfate | 10.0 | 10.0 |
| α-Amylase[5] | 1.0 | 1.0 |
| Protease[6] | 1.0 | 1.0 |

[1] A polyoxyethylene - polyoxypropylene copolymer (average molecular weight: 2,000)
[2] A product obtained by adding to a C12–C14 sec-alcohol ethylene oxide (7 mol) and propylene oxide (8.5 mol)
[3] JIS No. 2 sodium silicate
[4] An acrylic acid - maleic acid copolymer
[5] Duramyl 60T ™ (product of Novozymes)
[6] Granules (6 PU/g) prepared from each of the purified samples of the alkaline protease of an embodiment of the present invention shown in Table 1 according to the method described in Example 1 of Japanese Patent Application Laid-Open (kokai) No. 62-257990

Example 8

A detergent composition for hard surfaces (detergent J) was prepared from components shown in the below-described Table 5.

TABLE 5

| Components | Detergent J (mass %) |
|---|---|
| Anionic surfactant[1] | 15.0 |
| Nonionic surfactant[2] | 5.0 |
| Nonionic surfactant[3] | 5.0 |
| Amphoteric surfactant[4] | 7.5 |
| Amphoteric surfactant[5] | 4.0 |
| Citric acid | 1.0 |
| Polypropylene glycol[6] | 2.0 |
| Ethanol | 5.0 |

TABLE 5-continued

| | |
|---|---|
| Protease[7] | 1.0 |
| Perfume, water, etc./pH adjusting agent | 54.5 |
| Total | 100.0 |

[1] Sodium polyoxyethylene (EOP = 4) alkyl (C12) ether sulfate
[2] Polyoxyethylene (EOP = 8) alkyl (C12) ether
[3] Alkyl (C12) polyglucoside (condensation degree: 1.3)
[4] Mono long-chain tertiary alkyl (C12) dimethylamine oxide
[5] Alkyl (C12) hydroxydimethyl sulfobetaine
[6] Molecular weight: 10,000
[7] Each of the purified samples of the alkaline protease of an embodiment of the present invention shown in Table 1 (15 PU/mL)

Example 9

Granular detergents shown in the below-described Table 6 were prepared by using the aforementioned detergent A (see Example 3).

TABLE 6

| Components (mass %) | Detergent K | Detergent L | Detergent M | Detergent N |
|---|---|---|---|---|
| Detergent base of Example 3 | 98.4 | 98.3 | 98.5 | 97.2 |
| Perfume | 0.5 | 0.5 | 0.5 | 0.5 |
| Protease[1] | 0.5 | 0.5 | 0.5 | 0.5 |
| Conventional protease[2] | 0.6 | | | 0.6 |
| Cellulase[3] | | 0.7 | | 0.7 |
| Lipase[4] | | | 0.5 | 0.5 |

[1] Granules (6 PU/g) prepared from each of the purified samples of the alkaline protease of an embodiment of the present invention shown in Table 1 according to the method described in Example 1 of Japanese Patent Application Laid-Open (kokai) No. 62-257990
[2] Protease K-16 described in Japanese Patent Application Laid-Open (kokai) No. 5-25492, the activity thereof being regulated to 5 PU/g by according to the method described in Example 1 of Japanese Patent Application Laid-Open (kokai) No. 62-257990
[3] KAC-500 (product of Kao Corporation)
[4] Lipolase 100T ™ (product of Novozymes)

INDUSTRIAL APPLICABILITY

According to the present invention, an alkaline protease increased in production can be produced. In particular, there can be efficiently produced an alkaline protease having an activity even in the presence of a fatty acid of high concentration and exhibiting excellent detergency against complex soils containing proteins and sebum.

The invention claimed is:

1. An isolated DNA encoding an alkaline protease comprising a modified prepro amino acid sequence region and a mature alkaline protease amino acid sequence region wherein the unmodified prepro sequence is at least 95% homologous to SEQ ID NO:1 and said modified prepro amino acid sequence comprises one or more amino acid substitutions at positions corresponding to positions 52, 75, and 142 in the amino acid sequence set forth in SEQ ID NO:1 wherein said one or more substitutions improve the recovery of secreted and activated mature proteases fused to such a modified prepro region when the alkaline protease-encoding DNA is expressed in a *Bacillus* host cell and the substitutions are selected from the group consisting of:
   a substitution of aspartic acid or arginine for the amino acid at the position corresponding to position 52 of SEQ ID NO:1,
   a substitution of alanine or arginine for the amino acid at the position corresponding to position 75 of SEQ ID NO:1, and
   a substitution of lysine for the amino acid at the position corresponding to position 142 of SEQ ID NO:1,
wherein said improved recovery is compared to the recovery obtained in the absence of said amino acid substitutions at positions corresponding to positions 52, 75, and 142 of SEQ ID NO:1,
and wherein the mature alkaline protease amino acid sequence region comprises the amino acid sequence set forth in SEQ ID NO:2 or an amino acid sequence having at least 80% homology to the amino acid sequence set forth in SEQ ID NO:2.

2. A recombinant vector comprising the DNA as recited in claim 1.

3. A transformed bacterial host cell comprising the vector as recited in claim 2.

4. The transformed host cell according to claim 3, wherein the host cell is a *Bacillus* host cell.

5. An isolated DNA encoding a mutant prepro sequence comprising a modified prepro amino acid sequence region and a mature alkaline protease amino acid sequence region, wherein the unmodified prepro sequence is at least 95% homologous to SEQ ID NO:1 and said modified prepro amino acid sequence comprises one or more amino acid substitutions at positions corresponding to positions 52, 75, and 142 in the amino acid sequence set forth in SEQ ID NO:1 wherein said one or more substitutions improve the recovery of secreted and activated mature proteases fused to such a modified prepro region when the alkaline protease-encoding DNA is expressed in a *Bacillus* host cell and the substitutions are selected from the group consisting of:
   a substitution of aspartic acid or arginine for the amino acid at the position corresponding to position 52 of SEQ ID NO:1,
   a substitution of alanine or arginine for the amino acid at the position corresponding to position 75 of SEQ ID NO:1, and
   a substitution of lysine for the amino acid at the position corresponding to position 142 of SEQ ID NO:1,
wherein said improved recovery is compared to the recovery obtained in the absence of said amino acid substitutions at positions corresponding to positions 52, 75, and 142 of SEQ ID NO:1.

6. A method for producing an alkaline protease having the amino acid sequence of SEQ ID NO:2, or an amino acid sequence having at least 80% homology to the amino acid sequence set forth in SEQ ID NO:2, which method comprises culturing the transformed host cell as recited in claim 4 under conditions suitable for the expression of the protease and recovering the alkaline protease from the culture medium.

* * * * *

SEQUENCE LISTING

<160> NUMBER OF SEQ ID NOS: 16

<210> SEQ ID NO 1
<211> LENGTH: 206
<212> TYPE: PRT
<213> ORGANISM: Bacillus sp. KSM-KP43

<400> SEQUENCE: 1

```
Met Arg Lys Lys Lys Val Phe Leu Ser Val Leu Ser Ala Ala Ala
1               5                   10                  15

Ile Leu Ser Thr Val Ala Leu Ser Asn Pro Ser Ala Gly Gly Ala Arg
                20                  25                  30

Asn Phe Asp Leu Asp Phe Lys Gly Ile Gln Thr Thr Thr Asp Ala Lys
            35                  40                  45

Gly Phe Ser Lys Gln Gly Gln Thr Gly Ala Ala Ala Phe Leu Val Glu
        50                  55                  60

Ser Glu Asn Val Lys Leu Pro Lys Gly Leu Gln Lys Lys Leu Glu Thr
65                  70                  75                  80

Val Pro Ala Asn Asn Lys Leu His Ile Ile Gln Phe Asn Gly Pro Ile
                85                  90                  95

Leu Glu Glu Thr Lys Gln Gln Leu Glu Lys Thr Gly Ala Lys Ile Leu
                100                 105                 110

Asp Tyr Ile Pro Asp Tyr Ala Tyr Ile Val Glu Tyr Glu Gly Asp Val
            115                 120                 125

Lys Ser Ala Thr Ser Thr Ile Glu His Val Glu Ser Val Glu Pro Tyr
        130                 135                 140

Leu Pro Ile Tyr Arg Ile Asp Pro Gln Leu Phe Thr Lys Gly Ala Ser
145                 150                 155                 160

Glu Leu Val Lys Ala Val Ala Leu Asp Thr Lys Gln Lys Asn Lys Glu
```

```
                       165                 170                 175
Val Gln Leu Arg Gly Ile Glu Gln Ile Ala Gln Phe Ala Ile Ser Asn
            180                 185                 190

Asp Val Leu Tyr Ile Thr Ala Lys Pro Glu Tyr Lys Val Met
            195                 200                 205

<210> SEQ ID NO 2
<211> LENGTH: 434
<212> TYPE: PRT
<213> ORGANISM: Bacillus sp. KSM-KP43

<400> SEQUENCE: 2

Asn Asp Val Ala Arg Gly Ile Val Lys Ala Asp Val Ala Gln Ser Ser
1               5                   10                  15

Tyr Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
    50                  55                  60

Thr Asn Gly His Gly Thr His Val Ala Gly Ser Val Leu Gly Asn Gly
65                  70                  75                  80

Ser Thr Asn Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
            100                 105                 110

Thr Leu Phe Ser Gln Ala Tyr Ser Ala Gly Ala Arg Ile His Thr Asn
        115                 120                 125

Ser Trp Gly Ala Ala Val Asn Gly Ala Tyr Thr Thr Asp Ser Arg Asn
    130                 135                 140

Val Asp Asp Tyr Val Arg Lys Asn Asp Met Thr Ile Leu Phe Ala Ala
145                 150                 155                 160

Gly Asn Glu Gly Pro Asn Gly Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Tyr Ala Asp Asn Ile Asn His Val Ala Gln Phe Ser Ser Arg
        195                 200                 205

Gly Pro Thr Lys Asp Gly Arg Ile Lys Pro Asp Val Met Ala Pro Gly
    210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Val Lys Asn Arg Gly Ile Thr Pro Lys Pro Ser Leu Leu Lys Ala Ala
        275                 280                 285

Leu Ile Ala Gly Ala Ala Asp Ile Gly Leu Gly Tyr Pro Asn Gly Asn
    290                 295                 300

Gln Gly Trp Gly Arg Val Thr Leu Asp Lys Ser Leu Asn Val Ala Tyr
305                 310                 315                 320

Val Asn Glu Ser Ser Ser Leu Ser Thr Ser Gln Lys Ala Thr Tyr Ser
                325                 330                 335
```

-continued

```
Phe Thr Ala Thr Ala Gly Lys Pro Leu Lys Ile Ser Leu Val Trp Ser
                340                 345                 350

Asp Ala Pro Ala Ser Thr Thr Ala Ser Val Thr Leu Val Asn Asp Leu
            355                 360                 365

Asp Leu Val Ile Thr Ala Pro Asn Gly Thr Gln Tyr Val Gly Asn Asp
        370                 375                 380

Phe Thr Ser Pro Tyr Asn Asp Asn Trp Asp Gly Arg Asn Asn Val Glu
385                 390                 395                 400

Asn Val Phe Ile Asn Ala Pro Gln Ser Gly Thr Tyr Thr Ile Glu Val
                405                 410                 415

Gln Ala Tyr Asn Val Pro Val Gly Pro Gln Thr Phe Ser Leu Ala Ile
            420                 425                 430

Val Asn

<210> SEQ ID NO 3
<211> LENGTH: 1923
<212> TYPE: DNA
<213> ORGANISM: Bacillus sp. KSM-KP43
<220> FEATURE:
<221> NAME/KEY: CDS
<222> LOCATION: (1)..(1920)
<223> OTHER INFORMATION:

<400> SEQUENCE: 3 atg aga aag aag aaa aag gtg ttt tta tct gtt tta tca gct gca gcg     48
Met Arg Lys Lys Lys Lys Val Phe Leu Ser Val Leu Ser Ala Ala Ala
1               5                   10                  15 att ttg tcg act gtt gcg tta agt aat cca tct gca ggt ggt gca agg     96
Ile Leu Ser Thr Val Ala Leu Ser Asn Pro Ser Ala Gly Gly Ala Arg
                20                  25                  30 aat ttt gat ctg gat ttc aaa gga att cag aca aca act gat gct aaa    144
Asn Phe Asp Leu Asp Phe Lys Gly Ile Gln Thr Thr Thr Asp Ala Lys
            35                  40                  45 ggt ttc tcc aag cag ggg cag act ggt gct gct gct ttt ctg gtg gaa    192
Gly Phe Ser Lys Gln Gly Gln Thr Gly Ala Ala Ala Phe Leu Val Glu
        50                  55                  60 tct gaa aat gtg aaa ctc cca aaa ggt ttg cag aag aag ctt gaa aca    240
Ser Glu Asn Val Lys Leu Pro Lys Gly Leu Gln Lys Lys Leu Glu Thr
65                  70                  75                  80 gtc ccg gca aat aat aaa ctc cat att atc caa ttc aat gga cca att    288
Val Pro Ala Asn Asn Lys Leu His Ile Ile Gln Phe Asn Gly Pro Ile
                85                  90                  95 tta gaa gaa aca aaa cag cag ctg gaa aaa aca ggg gca aag att ctc    336
Leu Glu Glu Thr Lys Gln Gln Leu Glu Lys Thr Gly Ala Lys Ile Leu
                100                 105                 110 gac tac ata cct gat tat gct tac att gtc gag tat gag ggc gat gtt    384
Asp Tyr Ile Pro Asp Tyr Ala Tyr Ile Val Glu Tyr Glu Gly Asp Val
            115                 120                 125 aag tca gca aca agc acc att gag cac gtg gaa tcc gtg gag cct tat    432
Lys Ser Ala Thr Ser Thr Ile Glu His Val Glu Ser Val Glu Pro Tyr
        130                 135                 140 ttg ccg ata tac aga ata gat ccc cag ctt ttc aca aaa ggg gca tca    480
Leu Pro Ile Tyr Arg Ile Asp Pro Gln Leu Phe Thr Lys Gly Ala Ser
145                 150                 155                 160 gag ctt gta aaa gca gtg gcg ctt gat aca aag cag aaa aat aaa gag    528
Glu Leu Val Lys Ala Val Ala Leu Asp Thr Lys Gln Lys Asn Lys Glu
                165                 170                 175 gtg caa tta aga ggc atc gaa caa atc gca caa ttc gca ata agc aat    576
Val Gln Leu Arg Gly Ile Glu Gln Ile Ala Gln Phe Ala Ile Ser Asn
            180                 185                 190
```

```
gat gtg cta tat att acg gca aag cct gag tat aag gtg atg aat gat    624
Asp Val Leu Tyr Ile Thr Ala Lys Pro Glu Tyr Lys Val Met Asn Asp
            195                 200                 205 gtt gcg cgt gga att gtc aaa gcg gat gtg gct cag agc agc tac ggg    672
Val Ala Arg Gly Ile Val Lys Ala Asp Val Ala Gln Ser Ser Tyr Gly
210                 215                 220 ttg tat gga caa gga cag atc gta gcg gtt gcc gat aca ggg ctt gat    720
Leu Tyr Gly Gln Gly Gln Ile Val Ala Val Ala Asp Thr Gly Leu Asp
225                 230                 235                 240 aca ggt cgc aat gac agt tcg atg cat gaa gcc ttc cgc ggg aaa att    768
Thr Gly Arg Asn Asp Ser Ser Met His Glu Ala Phe Arg Gly Lys Ile
            245                 250                 255 act gca tta tat gca ttg gga cgg acg aat aat gcc aat gat acg aat    816
Thr Ala Leu Tyr Ala Leu Gly Arg Thr Asn Asn Ala Asn Asp Thr Asn
            260                 265                 270 ggt cat ggt acg cat gtg gct ggc tcc gta tta gga aac ggc tcc act    864
Gly His Gly Thr His Val Ala Gly Ser Val Leu Gly Asn Gly Ser Thr
            275                 280                 285 aat aaa gga atg gcg cct cag gcg aat cta gtc ttc caa tct atc atg    912
Asn Lys Gly Met Ala Pro Gln Ala Asn Leu Val Phe Gln Ser Ile Met
290                 295                 300 gat agc ggt ggg gga ctt gga gga cta cct tcg aat ctg caa acc tta    960
Asp Ser Gly Gly Gly Leu Gly Gly Leu Pro Ser Asn Leu Gln Thr Leu
305                 310                 315                 320 ttc agc caa gca tac agt gct ggt gcc aga att cat aca aac tcc tgg   1008
Phe Ser Gln Ala Tyr Ser Ala Gly Ala Arg Ile His Thr Asn Ser Trp
            325                 330                 335 gga gca gca gtg aat ggg gct tac aca aca gat tcc aga aat gtg gat   1056
Gly Ala Ala Val Asn Gly Ala Tyr Thr Thr Asp Ser Arg Asn Val Asp
            340                 345                 350 gac tat gtg cgc aaa aat gat atg acg atc ctt ttc gct gcc ggg aat   1104
Asp Tyr Val Arg Lys Asn Asp Met Thr Ile Leu Phe Ala Ala Gly Asn
            355                 360                 365 gaa gga ccg aac ggc gga acc atc agt gca cca ggc aca gct aaa aat   1152
Glu Gly Pro Asn Gly Gly Thr Ile Ser Ala Pro Gly Thr Ala Lys Asn
370                 375                 380 gca ata aca gtc gga gct acg gaa aac ctc cgc cca agc ttt ggg tct   1200
Ala Ile Thr Val Gly Ala Thr Glu Asn Leu Arg Pro Ser Phe Gly Ser
385                 390                 395                 400 tat gcg gac aat atc aac cat gtg gca cag ttc tct tca cgt gga ccg   1248
Tyr Ala Asp Asn Ile Asn His Val Ala Gln Phe Ser Ser Arg Gly Pro
            405                 410                 415 aca aag gat gga cgg atc aaa ccg gat gtc atg gca ccg gga acg ttc   1296
Thr Lys Asp Gly Arg Ile Lys Pro Asp Val Met Ala Pro Gly Thr Phe
            420                 425                 430 ata cta tca gca aga tct tct ctt gca ccg gat tcc tcc ttc tgg gcg   1344
Ile Leu Ser Ala Arg Ser Ser Leu Ala Pro Asp Ser Ser Phe Trp Ala
            435                 440                 445 aac cat gac agt aaa tat gca tac atg ggt gga acg tcc atg gct aca   1392
Asn His Asp Ser Lys Tyr Ala Tyr Met Gly Gly Thr Ser Met Ala Thr
450                 455                 460 ccg atc gtt gct gga aac gtg gca cag ctt cgt gag cat ttt gtg aaa   1440
Pro Ile Val Ala Gly Asn Val Ala Gln Leu Arg Glu His Phe Val Lys
465                 470                 475                 480 aac aga ggc atc aca cca aag cct tct cta tta aaa gcg gca ctg att   1488
Asn Arg Gly Ile Thr Pro Lys Pro Ser Leu Leu Lys Ala Ala Leu Ile
            485                 490                 495 gcc ggt gca gct gac atc ggc ctt ggc tac ccg aac ggt aac caa gga   1536
Ala Gly Ala Ala Asp Ile Gly Leu Gly Tyr Pro Asn Gly Asn Gln Gly
```

-continued

```
                         500                 505                 510
tgg gga cga gtg aca ttg gat aaa tcc ctg aac gtt gcc tat gtg aac      1584
Trp Gly Arg Val Thr Leu Asp Lys Ser Leu Asn Val Ala Tyr Val Asn
            515                 520                 525 gag tcc agt tct cta tcc acc agc caa aaa gcg acg tac tcg ttt act      1632
Glu Ser Ser Ser Leu Ser Thr Ser Gln Lys Ala Thr Tyr Ser Phe Thr
530                 535                 540 gct act gcc ggc aag cct ttg aaa atc tcc ctg gta tgg tct gat gcc      1680
Ala Thr Ala Gly Lys Pro Leu Lys Ile Ser Leu Val Trp Ser Asp Ala
545                 550                 555                 560 cct gcg agc aca act gct tcc gta acg ctt gtc aat gat ctg gac ctt      1728
Pro Ala Ser Thr Thr Ala Ser Val Thr Leu Val Asn Asp Leu Asp Leu
                565                 570                 575 gtc att acc gct cca aat ggc aca cag tat gta gga aat gac ttt act      1776
Val Ile Thr Ala Pro Asn Gly Thr Gln Tyr Val Gly Asn Asp Phe Thr
            580                 585                 590 tcg cca tac aat gat aac tgg gat ggc cgc aat aac gta gaa aat gta      1824
Ser Pro Tyr Asn Asp Asn Trp Asp Gly Arg Asn Asn Val Glu Asn Val
        595                 600                 605 ttt att aat gca cca caa agc ggg acg tat aca att gag gta cag gct      1872
Phe Ile Asn Ala Pro Gln Ser Gly Thr Tyr Thr Ile Glu Val Gln Ala
    610                 615                 620 tat aac gta ccg gtt gga cca cag acc ttc tcg ttg gca att gtg aat      1920
Tyr Asn Val Pro Val Gly Pro Gln Thr Phe Ser Leu Ala Ile Val Asn
625                 630                 635                 640 taa                                                                  1923
```

<210> SEQ ID NO 4
<211> LENGTH: 640
<212> TYPE: PRT
<213> ORGANISM: Bacillus sp. KSM-KP43

<400> SEQUENCE: 4

```
Met Arg Lys Lys Lys Val Phe Leu Ser Val Leu Ser Ala Ala Ala
1               5                  10                  15

Ile Leu Ser Thr Val Ala Leu Ser Asn Pro Ser Ala Gly Gly Ala Arg
            20                  25                  30

Asn Phe Asp Leu Asp Phe Lys Gly Ile Gln Thr Thr Thr Asp Ala Lys
        35                  40                  45

Gly Phe Ser Lys Gln Gly Gln Thr Gly Ala Ala Ala Phe Leu Val Glu
    50                  55                  60

Ser Glu Asn Val Lys Leu Pro Lys Gly Leu Gln Lys Lys Leu Glu Thr
65                  70                  75                  80

Val Pro Ala Asn Asn Lys Leu His Ile Ile Gln Phe Asn Gly Pro Ile
                85                  90                  95

Leu Glu Glu Thr Lys Gln Gln Leu Glu Lys Thr Gly Ala Lys Ile Leu
            100                 105                 110

Asp Tyr Ile Pro Asp Tyr Ala Tyr Ile Val Glu Tyr Glu Gly Asp Val
        115                 120                 125

Lys Ser Ala Thr Ser Thr Ile Glu His Val Glu Ser Val Glu Pro Tyr
    130                 135                 140

Leu Pro Ile Tyr Arg Ile Asp Pro Gln Leu Phe Thr Lys Gly Ala Ser
145                 150                 155                 160

Glu Leu Val Lys Ala Val Ala Leu Asp Thr Lys Gln Lys Asn Lys Glu
                165                 170                 175

Val Gln Leu Arg Gly Ile Glu Gln Ile Ala Gln Phe Ala Ile Ser Asn
            180                 185                 190
```

-continued

```
Asp Val Leu Tyr Ile Thr Ala Lys Pro Glu Tyr Lys Val Met Asn Asp
            195                 200                 205
Val Ala Arg Gly Ile Val Lys Ala Asp Val Ala Gln Ser Ser Tyr Gly
        210                 215                 220
Leu Tyr Gly Gln Gly Gln Ile Val Ala Val Ala Asp Thr Gly Leu Asp
225                 230                 235                 240
Thr Gly Arg Asn Asp Ser Ser Met His Glu Ala Phe Arg Gly Lys Ile
                245                 250                 255
Thr Ala Leu Tyr Ala Leu Gly Arg Thr Asn Asn Ala Asn Asp Thr Asn
            260                 265                 270
Gly His Gly Thr His Val Ala Gly Ser Val Leu Gly Asn Gly Ser Thr
        275                 280                 285
Asn Lys Gly Met Ala Pro Gln Ala Asn Leu Val Phe Gln Ser Ile Met
290                 295                 300
Asp Ser Gly Gly Leu Gly Gly Leu Pro Ser Asn Leu Gln Thr Leu
305                 310                 315                 320
Phe Ser Gln Ala Tyr Ser Ala Gly Ala Arg Ile His Thr Asn Ser Trp
                325                 330                 335
Gly Ala Ala Val Asn Gly Ala Tyr Thr Thr Asp Ser Arg Asn Val Asp
            340                 345                 350
Asp Tyr Val Arg Lys Asn Asp Met Thr Ile Leu Phe Ala Ala Gly Asn
        355                 360                 365
Glu Gly Pro Asn Gly Gly Thr Ile Ser Ala Pro Gly Thr Ala Lys Asn
370                 375                 380
Ala Ile Thr Val Gly Ala Thr Glu Asn Leu Arg Pro Ser Phe Gly Ser
385                 390                 395                 400
Tyr Ala Asp Asn Ile Asn His Val Ala Gln Phe Ser Ser Arg Gly Pro
                405                 410                 415
Thr Lys Asp Gly Arg Ile Lys Pro Asp Val Met Ala Pro Gly Thr Phe
            420                 425                 430
Ile Leu Ser Ala Arg Ser Ser Leu Ala Pro Asp Ser Ser Phe Trp Ala
        435                 440                 445
Asn His Asp Ser Lys Tyr Ala Tyr Met Gly Gly Thr Ser Met Ala Thr
450                 455                 460
Pro Ile Val Ala Gly Asn Val Ala Gln Leu Arg Glu His Phe Val Lys
465                 470                 475                 480
Asn Arg Gly Ile Thr Pro Lys Pro Ser Leu Leu Lys Ala Ala Leu Ile
                485                 490                 495
Ala Gly Ala Ala Asp Ile Gly Leu Gly Tyr Pro Asn Gly Asn Gln Gly
            500                 505                 510
Trp Gly Arg Val Thr Leu Asp Lys Ser Leu Asn Val Ala Tyr Val Asn
        515                 520                 525
Glu Ser Ser Ser Leu Ser Thr Ser Gln Lys Ala Thr Tyr Ser Phe Thr
530                 535                 540
Ala Thr Ala Gly Lys Pro Leu Lys Ile Ser Leu Val Trp Ser Asp Ala
545                 550                 555                 560
Pro Ala Ser Thr Thr Ala Ser Val Thr Leu Val Asn Asp Leu Asp Leu
                565                 570                 575
Val Ile Thr Ala Pro Asn Gly Thr Gln Tyr Val Gly Asn Asp Phe Thr
            580                 585                 590
Ser Pro Tyr Asn Asp Asn Trp Asp Gly Arg Asn Asn Val Glu Asn Val
        595                 600                 605
```

```
Phe Ile Asn Ala Pro Gln Ser Gly Thr Tyr Thr Ile Glu Val Gln Ala
    610                 615                 620

Tyr Asn Val Pro Val Gly Pro Gln Thr Phe Ser Leu Ala Ile Val Asn
625                 630                 635                 640
```

<210> SEQ ID NO 5
<211> LENGTH: 33
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (16)..(18)
<223> OTHER INFORMATION: n = a, c, g, or t

<400> SEQUENCE: 5
gctaaaggtt tctccnnnca ggggcagact ggt                                33

<210> SEQ ID NO 6
<211> LENGTH: 33
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (16)..(18)
<223> OTHER INFORMATION: n = a, c, g, or t

<400> SEQUENCE: 6
ctcccaaaag gtttgnnnaa gaagcttgaa aca                                33

<210> SEQ ID NO 7
<211> LENGTH: 33
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (16)..(18)
<223> OTHER INFORMATION: n = a, c, g, or t

<400> SEQUENCE: 7
cacgtggaat ccgtgnnncc ttatttgccg ata                                33

<210> SEQ ID NO 8
<211> LENGTH: 205
<212> TYPE: PRT
<213> ORGANISM: Bacillus sp. KSM-KP860

<400> SEQUENCE: 8

```
Met Arg Lys Lys Val Phe Leu Ser Val Leu Ser Ala Ala Ala Ile
1               5                   10                  15

Leu Ser Thr Val Ala Leu Asn Asn Pro Ser Ala Gly Asp Ala Arg Thr
                20                  25                  30

Phe Asp Leu Asp Phe Lys Gly Ile Gln Thr Thr Thr Asp Val Ser Gly
            35                  40                  45

Phe Ser Lys Gln Arg Gln Thr Gly Ala Ala Ala Phe Leu Val Glu Ser
        50                  55                  60

Glu Asn Val Lys Leu Leu Lys Gly Leu Leu Lys Lys Leu Glu Thr Val
65                  70                  75                  80

Pro Ala Asn Asn Lys Leu His Ile Val Gln Phe Asn Gly Pro Ile Leu
                85                  90                  95
```

Glu Glu Thr Lys Gln Lys Leu Glu Thr Thr Gly Ala Lys Ile Leu Asp
            100                 105                 110

Tyr Ile Pro Asp Tyr Ala Tyr Ile Val Glu Tyr Glu Gly Asp Val Gln
            115                 120                 125

Ser Lys Val Arg Ser Ile Glu His Val Glu Ser Val Glu Pro Tyr Leu
            130                 135                 140

Pro Lys Tyr Lys Ile Asp Pro Gln Leu Phe Thr Lys Gly Ala Ser Thr
145                 150                 155                 160

Leu Val Lys Ala Leu Ala Leu Asp Thr Lys Gln Asn Asn Lys Glu Val
            165                 170                 175

Gln Leu Arg Gly Ile Glu Glu Ile Ala Gln Tyr Val Ala Ser Asn Asp
            180                 185                 190

Val His Tyr Ile Thr Ala Lys Pro Glu Tyr Lys Val Met
            195                 200                 205

<210> SEQ ID NO 9
<211> LENGTH: 206
<212> TYPE: PRT
<213> ORGANISM: Bacillus sp. KSM-KP9865

<400> SEQUENCE: 9

Met Arg Lys Lys Lys Val Phe Leu Ser Val Leu Ser Ala Ala Ala
1               5                   10                  15

Ile Leu Ser Thr Val Ala Leu Ser Asn Pro Ser Ala Gly Gly Ala Arg
            20                  25                  30

Asn Phe Asp Leu Asp Phe Lys Gly Ile Gln Thr Ile Thr Asp Ala Lys
            35                  40                  45

Gly Phe Ser Lys Gln Gly Gln Thr Gly Ala Ala Ala Phe Leu Val Glu
        50                  55                  60

Ser Glu Asn Val Lys Leu Pro Lys Gly Leu Gln Lys Lys Leu Glu Thr
65              70                  75                  80

Val Pro Ala Asn Asn Lys Leu His Ile Val Gln Phe Asn Gly Pro Ile
            85                  90                  95

Leu Glu Glu Thr Lys Gln Gln Leu Glu Lys Thr Gly Ala Lys Ile Leu
            100                 105                 110

Asp Tyr Ile Pro Asp Tyr Ala Tyr Ile Val Glu Tyr Glu Gly Asp Val
            115                 120                 125

Lys Ser Ala Thr Ser Thr Ile Glu Asp Val Glu Ser Val Glu Pro Tyr
            130                 135                 140

Leu Pro Ile Tyr Arg Ile Asp Pro Gln Leu Phe Thr Lys Gly Ala Ser
145                 150                 155                 160

Glu Leu Val Lys Ala Val Ala Leu Asp Thr Asn Gln Lys Asn Lys Glu
            165                 170                 175

Val Gln Leu Arg Gly Ile Glu Gln Ile Ala Gln Phe Ala Thr Ser Asn
            180                 185                 190

Asp Val Leu Tyr Ile Thr Ala Lys Pro Glu Tyr Lys Val Met
            195                 200                 205

<210> SEQ ID NO 10
<211> LENGTH: 434
<212> TYPE: PRT
<213> ORGANISM: Bacillus sp. KSM-KP860

<400> SEQUENCE: 10

Asn Asp Val Ala Arg Gly Ile Val Lys Ala Asp Val Ala Gln Ser Ser
1               5                   10                  15

```
Tyr Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
            35                  40                  45

Lys Ile Thr Ala Leu Tyr Ala Leu Gly Arg Thr Asn Asn Ala Asn Asp
            50                  55                  60

Thr Asn Gly His Gly Thr His Val Ala Gly Ser Val Leu Gly Asn Gly
 65                  70                  75                  80

Ala Thr Asn Lys Gly Met Ala Pro Gln Ala Asn Leu Val Phe Gln Ser
                85                  90                  95

Ile Met Asp Ser Ser Gly Gly Leu Gly Gly Leu Pro Ser Asn Leu Gln
            100                 105                 110

Thr Leu Phe Ser Gln Ala Phe Ser Ala Gly Ala Arg Ile His Thr Asn
            115                 120                 125

Ser Trp Gly Ala Ala Val Asn Gly Ala Tyr Thr Thr Asp Ser Arg Asn
            130                 135                 140

Val Asp Asp Tyr Val Arg Lys Asn Asp Met Thr Ile Leu Phe Ala Ala
145                 150                 155                 160

Gly Asn Glu Gly Pro Asn Gly Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Tyr Ala Asp Asn Ile Asn His Val Ala Gln Phe Ser Ser Arg
            195                 200                 205

Gly Pro Thr Lys Asp Gly Arg Ile Lys Pro Asp Val Met Ala Pro Gly
            210                 215                 220

Thr Tyr Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Val Lys Asn Arg Gly Ile Thr Pro Lys Pro Ser Leu Leu Lys Ala Ala
            275                 280                 285

Leu Ile Ala Gly Ala Ala Asp Val Gly Leu Gly Tyr Pro Asn Gly Asn
            290                 295                 300

Gln Gly Trp Gly Arg Val Thr Leu Asp Lys Ser Leu Asn Val Ala Tyr
305                 310                 315                 320

Val Asn Glu Ser Ser Ala Leu Ser Thr Ser Gln Lys Ala Thr Tyr Thr
                325                 330                 335

Phe Thr Ala Thr Ala Gly Lys Pro Leu Lys Ile Ser Leu Val Trp Ser
            340                 345                 350

Asp Ala Pro Ala Ser Thr Thr Ala Ser Val Thr Leu Val Asn Asp Leu
            355                 360                 365

Asp Leu Val Ile Thr Ala Pro Asn Gly Thr Arg Tyr Val Gly Asn Asp
            370                 375                 380

Phe Ser Ala Pro Phe Asp Asn Asn Trp Asp Gly Arg Asn Asn Val Glu
385                 390                 395                 400

Asn Val Phe Ile Asn Ser Pro Gln Ser Gly Thr Tyr Thr Ile Glu Val
                405                 410                 415

Gln Ala Tyr Asn Val Pro Val Gly Pro Gln Asn Phe Ser Leu Ala Ile
            420                 425                 430
```

Val Asn

<210> SEQ ID NO 11
<211> LENGTH: 434
<212> TYPE: PRT
<213> ORGANISM: Bacillus sp. KSM-KP9865

<400> SEQUENCE: 11

```
Asn Asp Val Ala Arg Gly Ile Val Lys Ala Asp Val Ala Gln Ser Ser
1               5                  10                  15

Tyr Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
50                  55                  60

Thr Asn Gly His Gly Thr His Val Ala Gly Ser Val Leu Gly Asn Gly
65                  70                  75                  80

Ser Thr Asn Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
                100                 105                 110

Thr Leu Phe Ser Gln Ala Tyr Ser Ala Gly Ala Arg Ile His Thr Asn
            115                 120                 125

Ser Trp Gly Ala Ala Val Asn Gly Ala Tyr Thr Thr Asp Ser Arg Asn
130                 135                 140

Val Asp Asp Tyr Val Arg Lys Asn Asp Met Thr Ile Leu Phe Ala Ala
145                 150                 155                 160

Gly Asn Glu Gly Pro Asn Gly Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Tyr Ala Asp Asn Ile Asn His Val Ala Gln Phe Ser Ser Arg
        195                 200                 205

Gly Pro Thr Lys Asp Gly Arg Ile Lys Pro Asp Val Met Ala Pro Gly
210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Val Lys Asn Arg Gly Ile Thr Pro Lys Pro Ser Leu Leu Lys Ala Ala
        275                 280                 285

Leu Ile Ala Gly Ala Ala Asp Ile Gly Leu Gly Tyr Pro Asn Gly Asn
290                 295                 300

Gln Gly Trp Gly Arg Val Thr Leu Asp Lys Ser Leu Asn Val Ala Tyr
305                 310                 315                 320

Val Asn Glu Ser Ser Ser Leu Ser Thr Ser Gln Lys Ala Thr Tyr Ser
                325                 330                 335

Phe Thr Ala Thr Ala Gly Lys Pro Leu Lys Ile Ser Leu Val Trp Ser
            340                 345                 350

Asp Ala Pro Ala Ser Thr Thr Ala Ser Val Thr Leu Val Asn Asp Leu
        355                 360                 365
```

-continued

```
Asp Leu Val Ile Thr Ala Pro Asn Gly Thr Gln Tyr Val Gly Asn Asp
    370                 375                 380

Phe Thr Ser Pro Tyr Asn Asn Asn Trp Asp Gly Arg Asn Asn Val Glu
385                 390                 395                 400

Asn Val Phe Ile Asn Ala Pro Gln Ser Gly Thr Tyr Thr Ile Glu Val
                405                 410                 415

Gln Ala Tyr Asn Val Pro Val Gly Pro Gln Thr Phe Ser Leu Ala Ile
                420                 425                 430

Val Asn

<210> SEQ ID NO 12
<211> LENGTH: 433
<212> TYPE: PRT
<213> ORGANISM: Bacillus No. D-6

<400> SEQUENCE: 12

Asn Asp Val Ala Arg Gly Ile Val Lys Ala Asp Val Ala Gln Asn Asn
1               5                   10                  15

Tyr Gly Leu Tyr Gly Gln Gly Gln Val Val Ala Val Ala Asp Thr Gly
                20                  25                  30

Leu Asp Thr Gly Arg Asn Asp Ser Ser Met His Glu Ala Phe Arg Gly
            35                  40                  45

Lys Ile Thr Ala Leu Tyr Ala Leu Gly Arg Thr Asn Asn Ala Asn Asp
50                  55                  60

Pro Asn Gly His Gly Thr His Val Ala Gly Ser Val Leu Gly Asn Ala
65                  70                  75                  80

Leu Asn Lys Gly Met Ala Pro Gln Ala Asn Leu Val Phe Gln Ser Ile
                85                  90                  95

Met Asp Ser Ser Gly Gly Leu Gly Gly Leu Pro Ser Asn Leu Asn Thr
                100                 105                 110

Leu Phe Ser Gln Ala Trp Asn Ala Gly Ala Arg Ile His Thr Asn Ser
            115                 120                 125

Trp Gly Ala Pro Val Asn Gly Ala Tyr Thr Ala Asn Ser Arg Gln Val
130                 135                 140

Asp Glu Tyr Val Arg Asn Asn Asp Met Thr Val Leu Phe Ala Ala Gly
145                 150                 155                 160

Asn Glu Gly Pro Asn Ser Gly Thr Ile Ser Ala Pro Gly Thr Ala Lys
                165                 170                 175

Asn Ala Ile Thr Val Gly Ala Thr Glu Asn Tyr Arg Pro Ser Phe Gly
            180                 185                 190

Ser Ile Ala Asp Asn Pro Asn His Ile Ala Gln Phe Ser Ser Arg Gly
        195                 200                 205

Ala Thr Arg Asp Gly Arg Ile Lys Pro Asp Val Thr Ala Pro Gly Thr
210                 215                 220

Phe Ile Leu Ser Ala Arg Ser Ser Leu Ala Pro Asp Ser Ser Phe Trp
225                 230                 235                 240

Ala Asn Tyr Asn Ser Lys Tyr Ala Tyr Met Gly Gly Thr Ser Met Ala
                245                 250                 255

Thr Pro Ile Val Ala Gly Asn Val Ala Gln Leu Arg Glu His Phe Ile
            260                 265                 270

Lys Asn Arg Gly Ile Thr Pro Lys Pro Ser Leu Ile Lys Ala Ala Leu
        275                 280                 285

Ile Ala Gly Ala Thr Asp Val Gly Leu Gly Tyr Pro Ser Gly Asp Gln
290                 295                 300
```

```
Gly Trp Gly Arg Val Thr Leu Asp Lys Ser Leu Asn Val Ala Tyr Val
305                 310                 315                 320

Asn Glu Ala Thr Ala Leu Thr Thr Gly Gln Lys Ala Thr Tyr Ser Phe
            325                 330                 335

Gln Thr Gln Ala Gly Lys Pro Leu Lys Ile Ser Leu Val Trp Thr Asp
        340                 345                 350

Ala Pro Gly Ser Thr Thr Ala Ser Tyr Thr Leu Val Asn Asp Leu Asp
    355                 360                 365

Leu Val Ile Thr Ala Pro Asn Gly Gln Lys Tyr Val Gly Asn Asp Phe
370                 375                 380

Ser Tyr Pro Tyr Asp Asn Asn Trp Asp Gly Arg Asn Asn Val Glu Asn
385                 390                 395                 400

Val Phe Ile Asn Ala Pro Gln Ser Gly Thr Tyr Thr Ile Glu Val Gln
                405                 410                 415

Ala Tyr Asn Val Pro Ser Gly Pro Gln Arg Phe Ser Leu Ala Ile Val
            420                 425                 430

His

<210> SEQ ID NO 13
<211> LENGTH: 433
<212> TYPE: PRT
<213> ORGANISM: Bacillus sp. Y

<400> SEQUENCE: 13

Asn Asp Val Ala Arg Gly Ile Val Lys Ala Asp Val Ala Gln Asn Asn
1               5                   10                  15

Tyr Gly Leu Tyr Gly Gln Gly Gln Val Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Ser Asp
50                  55                  60

Pro Asn Gly His Gly Thr His Val Ala Gly Ser Val Leu Gly Asn Ala
65                  70                  75                  80

Leu Asn Lys Gly Met Ala Pro Gln Ala Asn Leu Val Phe Gln Ser Ile
            85                  90                  95

Met Asp Ser Ser Gly Gly Leu Gly Gly Leu Pro Ser Asn Leu Asn Thr
            100                 105                 110

Leu Phe Ser Gln Ala Trp Asn Ala Gly Ala Arg Ile His Thr Asn Ser
        115                 120                 125

Trp Gly Ala Pro Val Asn Gly Ala Tyr Thr Ala Asn Ser Arg Gln Val
130                 135                 140

Asp Glu Tyr Val Arg Asn Asn Asp Met Thr Val Leu Phe Ala Ala Gly
145                 150                 155                 160

Asn Glu Gly Pro Asn Ser Gly Thr Ile Ser Ala Pro Gly Thr Ala Lys
                165                 170                 175

Asn Ala Ile Thr Val Gly Ala Thr Glu Asn Tyr Arg Pro Ser Phe Gly
            180                 185                 190

Ser Ile Ala Asp Asn Pro Asn His Ile Ala Gln Phe Ser Ser Arg Gly
        195                 200                 205

Ala Thr Arg Asp Gly Arg Ile Lys Pro Asp Val Thr Ala Pro Gly Thr
    210                 215                 220

Phe Ile Leu Ser Ala Arg Ser Ser Leu Ala Pro Asp Ser Ser Phe Trp
225                 230                 235                 240
```

```
Ala Asn Tyr Asn Ser Lys Tyr Ala Tyr Met Gly Gly Thr Ser Met Ala
                245                 250                 255

Thr Pro Ile Val Ala Gly Asn Val Ala Gln Leu Arg Glu His Phe Ile
            260                 265                 270

Lys Asn Arg Gly Ile Thr Pro Lys Pro Ser Leu Ile Lys Ala Ala Leu
        275                 280                 285

Ile Ala Gly Ala Thr Asp Val Gly Leu Gly Tyr Pro Asn Gly Asp Gln
    290                 295                 300

Gly Trp Gly Arg Val Thr Leu Asn Lys Ser Leu Asn Val Ala Tyr Val
305                 310                 315                 320

Asn Glu Ala Thr Ala Leu Ala Thr Gly Gln Lys Ala Thr Tyr Ser Phe
                325                 330                 335

Gln Ala Gln Ala Gly Lys Pro Leu Lys Ile Ser Leu Val Trp Thr Asp
            340                 345                 350

Ala Pro Gly Ser Thr Thr Ala Ser Tyr Thr Leu Val Asn Asp Leu Asp
        355                 360                 365

Leu Val Ile Thr Ala Pro Asn Gly Gln Lys Tyr Val Gly Asn Asp Phe
    370                 375                 380

Ser Tyr Pro Tyr Asp Asn Asn Trp Asp Gly Arg Asn Asn Val Glu Asn
385                 390                 395                 400

Val Phe Ile Asn Ala Pro Gln Ser Gly Thr Tyr Ile Ile Glu Val Gln
                405                 410                 415

Ala Tyr Asn Val Pro Ser Gly Pro Gln Arg Phe Ser Leu Ala Ile Val
            420                 425                 430

His

<210> SEQ ID NO 14
<211> LENGTH: 433
<212> TYPE: PRT
<213> ORGANISM: Bacillus SD521

<400> SEQUENCE: 14

Asn Asp Val Ala Arg Gly Ile Val Lys Ala Asp Val Ala Gln Asn Asn
1               5                   10                  15

Tyr Gly Leu Tyr Gly Gln Gly Gln Val Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
    50                  55                  60

Pro Asn Gly His Gly Thr His Val Ala Gly Ser Val Leu Gly Asn Ala
65                  70                  75                  80

Leu Asn Lys Gly Met Ala Pro Gln Ala Asn Leu Val Phe Gln Ser Ile
                85                  90                  95

Met Asp Ser Ser Gly Gly Leu Gly Leu Pro Ser Asn Leu Asn Thr
            100                 105                 110

Leu Phe Ser Gln Ala Trp Asn Ala Gly Ala Arg Ile His Thr Asn Ser
        115                 120                 125

Trp Gly Ala Pro Val Asn Gly Ala Tyr Thr Ala Asn Ser Arg Gln Val
    130                 135                 140

Asp Glu Tyr Val Arg Asn Asn Asp Met Thr Val Leu Phe Ala Ala Gly
145                 150                 155                 160

Asn Glu Gly Pro Asn Ser Gly Thr Ile Ser Ala Pro Gly Thr Ala Lys
                165                 170                 175
```

-continued

```
Asn Ala Ile Thr Val Gly Ala Thr Glu Asn Tyr Arg Pro Ser Phe Gly
            180                 185                 190

Ser Leu Ala Asp Asn Pro Asn His Ile Ala Gln Phe Ser Ser Arg Gly
        195                 200                 205

Ala Thr Arg Asp Gly Arg Ile Lys Pro Asp Val Thr Ala Pro Gly Thr
    210                 215                 220

Phe Ile Leu Ser Ala Arg Ser Ser Leu Ala Pro Asp Ser Ser Phe Trp
225                 230                 235                 240

Ala Asn Tyr Asn Ser Lys Tyr Ala Tyr Met Gly Gly Thr Ser Met Ala
                245                 250                 255

Thr Pro Ile Val Ala Gly Asn Val Ala Gln Leu Arg Glu His Phe Ile
            260                 265                 270

Lys Asn Arg Gly Ile Thr Pro Lys Pro Ser Leu Ile Lys Ala Ala Leu
        275                 280                 285

Ile Ala Gly Ala Thr Asp Val Gly Leu Gly Tyr Pro Ser Gly Asp Gln
    290                 295                 300

Gly Trp Gly Arg Val Thr Leu Asp Lys Ser Leu Asn Val Ala Tyr Val
305                 310                 315                 320

Asn Glu Ala Thr Ala Leu Ala Thr Gly Gln Lys Ala Thr Tyr Ser Phe
                325                 330                 335

Gln Ala Gln Ala Gly Lys Pro Leu Lys Ile Ser Leu Val Trp Thr Asp
            340                 345                 350

Ala Pro Gly Ser Thr Thr Ala Ser Tyr Thr Leu Val Asn Asp Leu Asp
        355                 360                 365

Leu Val Ile Thr Ala Pro Asn Gly Gln Lys Tyr Val Gly Asn Asp Phe
    370                 375                 380

Ser Tyr Pro Tyr Asp Asn Asn Trp Asp Gly Arg Asn Asn Val Glu Asn
385                 390                 395                 400

Val Phe Ile Asn Ala Pro Gln Ser Gly Thr Tyr Thr Ile Glu Val Gln
                405                 410                 415

Ala Tyr Asn Val Pro Ser Gly Pro Gln Arg Phe Ser Leu Ala Ile Val
            420                 425                 430

His
```

<210> SEQ ID NO 15
<211> LENGTH: 434
<212> TYPE: PRT
<213> ORGANISM: NCIB12289

<400> SEQUENCE: 15

```
Asn Asp Val Ala Arg Gly Ile Val Lys Ala Asp Val Ala Gln Ser Ser
1               5                   10                  15

Tyr Gly Leu Tyr Gly Gln Gly Gln Val Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Ile Tyr Ala Leu Gly Arg Thr Asn Asn Ala Asn Asp
    50                  55                  60

Pro Asn Gly His Gly Thr His Val Ala Gly Ser Val Leu Gly Asn Gly
65                  70                  75                  80

Thr Ser Asn Lys Gly Met Ala Pro Gln Ala Asn Leu Val Phe Gln Ser
                85                  90                  95

Val Met Asp Ser Asn Gly Gly Leu Gly Gly Leu Pro Ser Asn Val Ser
            100                 105                 110
```

```
Thr Leu Phe Ser Gln Ala Tyr Ser Ala Gly Ala Arg Ile His Thr Asn
        115                 120                 125

Ser Trp Gly Ala Pro Val Asn Gly Ala Tyr Thr Thr Asp Ser Arg Asn
        130                 135                 140

Val Asp Asp Tyr Val Arg Lys Asn Asp Met Ala Val Leu Phe Ala Ala
145                 150                 155                 160

Gly Asn Glu Gly Pro Asn Gly Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Tyr Ala Asp Asn Ile Asn His Val Ala Gln Phe Ser Ser Arg
            195                 200                 205

Gly Pro Thr Lys Asp Gly Arg Ile Lys Pro Asp Val Met Ala Pro Gly
        210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Ile Lys Asn Arg Gly Ile Thr Pro Lys Pro Ser Leu Leu Lys Ala Ala
        275                 280                 285

Leu Ile Ala Gly Ala Thr Asp Ile Gly Leu Gly Tyr Pro Ser Gly Asn
290                 295                 300

Gln Gly Trp Gly Arg Val Thr Leu Asp Lys Ser Leu Asn Val Ala Phe
305                 310                 315                 320

Val Asn Glu Thr Ser Ser Leu Ser Thr Asn Gln Lys Ala Thr Tyr Ser
                325                 330                 335

Phe Thr Ala Gln Ser Gly Lys Pro Leu Lys Ile Ser Leu Val Trp Ser
            340                 345                 350

Asp Ala Pro Ala Ser Thr Ser Ala Ser Val Thr Leu Val Asn Asp Leu
        355                 360                 365

Asp Leu Val Ile Thr Ala Pro Asn Gly Thr Lys Tyr Val Gly Asn Asp
        370                 375                 380

Phe Thr Ala Pro Tyr Asp Asn Asn Trp Asp Gly Arg Asn Asn Val Glu
385                 390                 395                 400

Asn Val Phe Ile Asn Ala Pro Gln Ser Gly Thr Tyr Thr Val Glu Val
                405                 410                 415

Gln Ala Tyr Asn Val Pro Gln Gly Pro Gln Ala Phe Ser Leu Ala Ile
            420                 425                 430

Val Asn

<210> SEQ ID NO 16
<211> LENGTH: 433
<212> TYPE: PRT
<213> ORGANISM: NCIB12513

<400> SEQUENCE: 16

Asn Asp Val Ala Arg Gly Ile Val Lys Ala Asp Val Ala Gln Asn Asn
1               5                   10                  15

Phe Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45
```

-continued

```
Lys Ile Thr Ala Leu Tyr Ala Leu Gly Arg Thr Asn Asn Ala Asn Asp
 50                  55                  60

Pro Asn Gly His Gly Thr His Val Ala Gly Ser Val Leu Gly Asn Ala
 65                  70                  75                  80

Thr Asn Lys Gly Met Ala Pro Gln Ala Asn Leu Val Phe Gln Ser Ile
                 85                  90                  95

Met Asp Ser Gly Gly Leu Gly Gly Leu Pro Ala Asn Leu Gln Thr
                100                 105                 110

Leu Phe Ser Gln Ala Tyr Ser Ala Gly Ala Arg Ile His Thr Asn Ser
            115                 120                 125

Trp Gly Ala Pro Val Asn Gly Ala Tyr Thr Thr Asp Ser Arg Asn Val
130                 135                 140

Asp Asp Tyr Val Arg Lys Asn Asp Met Thr Ile Leu Phe Ala Ala Gly
145                 150                 155                 160

Asn Glu Gly Pro Gly Ser Gly Thr Ile Ser Ala Pro Gly Thr Ala Lys
                165                 170                 175

Asn Ala Ile Thr Val Gly Ala Thr Glu Asn Leu Arg Pro Ser Phe Gly
            180                 185                 190

Ser Tyr Ala Asp Asn Ile Asn His Val Ala Gln Phe Ser Ser Arg Gly
            195                 200                 205

Pro Thr Arg Asp Gly Arg Ile Lys Pro Asp Val Met Ala Pro Gly Thr
210                 215                 220

Tyr Ile Leu Ser Ala Arg Ser Ser Leu Ala Pro Asp Ser Ser Phe Trp
225                 230                 235                 240

Ala Asn His Asp Ser Lys Tyr Ala Tyr Met Gly Gly Thr Ser Met Ala
                245                 250                 255

Thr Pro Ile Val Ala Gly Asn Val Ala Gln Leu Arg Glu His Phe Val
            260                 265                 270

Lys Asn Arg Gly Val Thr Pro Lys Pro Ser Leu Leu Lys Ala Ala Leu
            275                 280                 285

Ile Ala Gly Ala Ala Asp Val Gly Leu Gly Phe Pro Asn Gly Asn Gln
290                 295                 300

Gly Trp Gly Arg Val Thr Leu Asp Lys Ser Leu Asn Val Ala Phe Val
305                 310                 315                 320

Asn Glu Thr Ser Pro Leu Ser Thr Ser Gln Lys Ala Thr Tyr Ser Phe
                325                 330                 335

Thr Ala Gln Ala Gly Lys Pro Leu Lys Ile Ser Leu Val Trp Ser Asp
            340                 345                 350

Ala Pro Gly Ser Thr Thr Ala Ser Leu Thr Leu Val Asn Asp Leu Asp
            355                 360                 365

Leu Val Ile Thr Ala Pro Asn Gly Thr Lys Tyr Val Gly Asn Asp Phe
            370                 375                 380

Thr Ala Pro Tyr Asp Asn Asn Trp Asp Gly Arg Asn Asn Val Glu Asn
385                 390                 395                 400

Val Phe Ile Asn Ala Pro Gln Ser Gly Thr Tyr Thr Val Glu Val Gln
                405                 410                 415

Ala Tyr Asn Val Pro Val Ser Pro Gln Thr Phe Ser Leu Ala Ile Val
            420                 425                 430

His
```